(12) United States Patent
Hellmuth et al.

(10) Patent No.: US 12,173,261 B2
(45) Date of Patent: Dec. 24, 2024

(54) PROTEASE ENZYME VARIANTS AND USES THEREOF

(71) Applicant: AB Enzymes Oy, Rajamäki (FI)

(72) Inventors: Hendrik Hellmuth, Darmstadt (DE); Kari Juntunen, Rajamäki (FI); Marja Paloheimo, Rajamäki (FI); Leena Valtakari, Rajamäki (FI)

(73) Assignee: AB Enzymes Oy, Rajamäki (FI)

( * ) Notice: Subject to any disclaimer, the term of this patent is extended or adjusted under 35 U.S.C. 154(b) by 820 days.

(21) Appl. No.: 17/284,190

(22) PCT Filed: Oct. 10, 2019

(86) PCT No.: PCT/FI2019/050724
§ 371 (c)(1),
(2) Date: Apr. 9, 2021

(87) PCT Pub. No.: WO2020/074781
PCT Pub. Date: Apr. 16, 2020

(65) Prior Publication Data
US 2023/0046249 A1 Feb. 16, 2023

(30) Foreign Application Priority Data
Oct. 12, 2018 (EP) .................... 18200114

(51) Int. Cl.
*C11D 3/386* (2006.01)
*C12N 1/14* (2006.01)
*C12N 9/58* (2006.01)
*C12N 15/80* (2006.01)

(52) U.S. Cl.
CPC ............ *C11D 3/38618* (2013.01); *C12N 1/14* (2013.01); *C12N 9/58* (2013.01); *C12N 15/80* (2013.01); *C12Y 304/21* (2013.01); *C11D 2111/12* (2024.01); *C12N 2800/10* (2013.01)

(58) Field of Classification Search
CPC ..................................... C12N 9/58
See application file for complete search history.

(56) References Cited

U.S. PATENT DOCUMENTS

| | | |
|---|---|---|
| 3,652,399 A | 3/1972 | Isono et al. |
| 5,089,163 A | 2/1992 | Aronson et al. |
| 5,288,627 A | 2/1994 | Nielsen et al. |
| 5,612,306 A | 3/1997 | O'Brien |
| 5,770,418 A | 6/1998 | Yaver et al. |
| 5,843,745 A | 12/1998 | Berka et al. |
| 5,962,765 A | 10/1999 | St. Leger et al. |
| 6,300,116 B1 | 10/2001 | Von der Osten et al. |
| 6,573,086 B1 | 6/2003 | Emalfrab et al. |
| 6,682,924 B1 | 1/2004 | Sierkstra et al. |
| 9,404,164 B2 | 8/2016 | Valtakari et al. |
| 10,221,377 B2 | 3/2019 | Valtakari et al. |
| 2003/0228995 A1 | 12/2003 | Poulose et al. |
| 2004/0023355 A1 | 2/2004 | Sierkstra et al. |
| 2009/0163400 A1 | 6/2009 | Sierkstra et al. |
| 2010/0120649 A1 | 5/2010 | Andersen |
| 2011/0003729 A1 | 1/2011 | Juntunen et al. |
| 2011/0008870 A1 | 1/2011 | Makinen et al. |
| 2011/0028375 A1 | 2/2011 | Juntunen et al. |
| 2012/0107905 A1 | 5/2012 | Juntunen et al. |
| 2012/0252064 A1 | 10/2012 | Valtakari et al. |
| 2016/0376530 A1 | 12/2016 | Valtakari et al. |

FOREIGN PATENT DOCUMENTS

| | | |
|---|---|---|
| DE | 102012209289 | 12/2013 |
| EP | 0244234 | 11/1987 |
| EP | 0352244 | 1/1990 |
| EP | 0290567 | 6/1992 |
| EP | 0290569 | 6/1992 |
| EP | 0519229 | 12/1992 |
| EP | 0479870 | 10/2000 |
| EP | 1347045 | 9/2003 |
| EP | 1464626 A2 | 10/2004 |
| EP | 1870453 | 12/2007 |
| EP | 1009815 | 1/2008 |
| EP | 1464626 B1 | 11/2009 |
| EP | 2691520 | 3/2012 |
| EP | 2712915 | 4/2014 |
| WO | WO 1988/003946 | 6/1988 |
| WO | WO 1988/007581 | 10/1988 |
| WO | WO 1989/004361 | 5/1989 |
| WO | WO 1989/006270 | 7/1989 |

(Continued)

OTHER PUBLICATIONS

Anwar et al., "Alkaline proteases: A review," Bioresource Technology, Jun. 1998, 64:175-183.

Bailey et al., "Induction, isolation and testing of stable Trichoderma reesei mutants with improved production of solubilizing cellulase," Enzyme Microb. Technol., Apr. 1981, 3(2):153-157.

Chen et al., "The intramolecular chaperone-mediated protein folding," Curr. Opin. Struct. Biol., Dec. 2008, 18(6):765-770.

Cherry et al., "Directed evolution of industrial enzymes: an update," Curr. Opin. Biotechnol., Aug. 2003, 14(4):438-443.

(Continued)

*Primary Examiner* — Suzanne M Noakes
(74) *Attorney, Agent, or Firm* — Fish & Richardson P.C.

(57) ABSTRACT

The present invention is related to variants of fungal serine protease enzyme, which have serine protease activity of *Malbranchea* protease. Also disclosed are isolated nucleic acid molecules, comprising polynucleotide sequences which encode variants of fungal serine protease enzyme, nucleic acid sequences encoding said protease variants, a host cell and a process of producing polypeptides having serine protease activity. Said protease variants are useful as enzyme preparations applicable in detergent compositions and for treating fibers, wool, hair, leather, or silk, for treating food or feed, or for any applications involving modification, degradation or removal of proteinaceous material.

56 Claims, 10 Drawing Sheets
Specification includes a Sequence Listing.

(56) References Cited

FOREIGN PATENT DOCUMENTS

| WO | WO 1992/003529 | 3/1992 |
|---|---|---|
| WO | WO 1992/005239 | 4/1992 |
| WO | WO 1992/018599 | 10/1992 |
| WO | WO 1994/025583 | 11/1994 |
| WO | WO 1995/023221 | 8/1995 |
| WO | WO 1996/018722 | 6/1996 |
| WO | WO 1997/002753 | 1/1997 |
| WO | WO 1997/008325 | 3/1997 |
| WO | WO 1997/028243 | 8/1997 |
| WO | WO 1998/020116 | 5/1998 |
| WO | WO 1999/064555 | 12/1999 |
| WO | WO 2002/008398 | 1/2002 |
| WO | WO 2006/073839 | 7/2006 |
| WO | WO 2007/145963 | 12/2007 |
| WO | WO 2008/045148 | 4/2008 |
| WO | WO 2009/096916 | 8/2009 |
| WO | WO 2010/039840 | 4/2010 |
| WO | WO 2010/125174 | 11/2010 |
| WO | WO 2010/125175 | 11/2010 |
| WO | WO 2011/003968 | 1/2011 |
| WO | WO 2011/009700 | 1/2011 |
| WO | WO 2011/032988 | 3/2011 |
| WO | WO 2011/141358 | 11/2011 |
| WO | WO 2012/080201 | 6/2012 |
| WO | WO 2012/080202 | 6/2012 |
| WO | WO 2012/131023 | 10/2012 |
| WO | WO 2014/138983 | 9/2014 |
| WO | WO 2016/096714 | 6/2016 |
| WO | WO 2020/074781 | 4/2020 |

OTHER PUBLICATIONS

EP Search Report in European Appln. No. EP 18200114, dated Nov. 13, 2018, 2 pages.
Gaucher et al., "Thermomycolin," Handbook of Proteolytic Enzymes 2nd Ed., 2004, pp. 1834-1835.
Gupta et al., "An overview on fermentation, downstream processing and properties of microbial alkaline protease," Appl. Microbiol. Biotechnol., Dec. 2002, 60: 381-395.
Haakana et al., "Cloning of cellulase genes from Melanocarpus albomyces and their efficient expression in Trichoderma reesei," Enzyme Microb. Technol., Feb. 5, 2004, 34(2):159-167.
Joutsjoki et al., "Transformation of Trichoderma reesei with the Hormoconis resinae glucoamylase P (gamP) gene: production of a heterologous glucoamylase by Trichoderma reesei," Curr. Genet., Sep. 1993, 24:223-228.
Kalisz, "Microbial proteinases," Adv. Biochem. Eng. Biotechnol., 1988, 36:1-65.
Karhunen et al., "High frequency one-step gene replacement in Trichoderma reesei. I. Endoglucanase I overproduction," Mol. Gen. Genet., Dec. 1993, 241:515-522.
Malardier et al., "Cloning of the nitrate reductase gene (niaD) of Aspergillus nidulans and its use for transformation of Fusarium oxysporum," Gene, May 15, 1989, 78(1):147-156.
Martinez et al., "Genome sequencing and analysis of the biomass-degrading fungus Trichoderma reesei (syn. Hypocrea jecorina)," Nat. Biotech., May 2008, 26(5):553-560.
Maurer, "Detergent proteases," Curr. Opin. Biotechnol., Aug. 2004, 15(4):330-334.
Maurer, "Enzymes, Detergent," Encyclopedia of Industrial Biotechnology: Bioprocess, Bioseparation, and Cell Technology, Flickinger (ed.), John Wiley & Sons, Inc., Apr. 2010, pp. 1-17.
Ong et al., "Production, purification and characterization of thermomycolase, the extracellular serine protease of the thermophilic fungus Malbranchea pulchella var. sulfurea," Can. J. Microbiol., 1975, 22(2):165-176.
Paloheimo et al., "High-yield production of a bacterial xylanase in the filamentous fungus Trichoderma reesei requires a carrier polypeptide with an intact domain structure," Appl. Env. Microbiol., Dec. 2003, 69(12):7073-7082.

PCT International Preliminary Report and Written Opinion in International Appln. No. PCT/FI2019/050724, dated Apr. 8, 2021, 6 pages.
PCT International Search Report and Written Opinion in International Appln. No. PCT/FI2019/050724, dated Jan. 9, 2020, 16 pages.
Penttilä et al., "A versatile transformation system for the cellulolytic filamentous fungus Trichoderma reesei," Gene, 1987, 61(2):155-164.
Rao et al., "Molecular and biotechnological aspects of microbial proteases," Microbiol. Mol. Biol. Rev., Sep. 1998, 62(3):597-635.
Abu-Shady et al., "Production, Partial Purification and Some Properties of Thermostable Alkaline Protease from Malbranchea sulfurea and its Compatibility with Commercial Detergents," Afr. J. Mycol. and Biotech., 2001, 9(3):17-26.
Altschul et al., "Basic Local Alignment Search Tool," J. Mol. Biol., 1990, 215:403-410.
AMFPE.org [online], "AMFEP List of Commercial Enzymes," Association of Manufacturers and Formulators of Enzyme products, Oct. 2009, at URL: <http://www.amfep.org/list.html>, 8 pages.
Antal et al., "Colony growth, in vitro antagonism and secretion of extracellular enzymes in cold-tolerant strains of Trichoderma species," Mycol. Res., 2000, 5:545-549.
Banerjee et al., "Thermostable alkaline protease from Bacillus brevis and its characterization as a laundry detergent additive," Process Biochemistry, Oct. 1999, 35(1-2):213-219.
Beg et al., "Purification and characterization of an oxidation-stable, thiol-dependent serine alkaline protease from Bacillus mojavensis," Enzyme and Microbial Technology, 2003, 32:294-304.
Bolton et al., "A General Method for the Isolation of RNA Complementary to DNA," Proc. Nat. Acad. Sci. USA, 1962, 48:1390-1397.
Branden et al., "Introduction to Protein Structure," 2nd edition, Garland Science Publisher, Jan. 1999, pp. 3-12, 11 pages.
D'Acunzo et al., "Oxidation of phenols by laccase and laccase-mediator systems," Eur. J. Biochem., 2002, 269:5330-5335.
Dienes et al., "Identification of a trypsin-like serine protease from Trichoderma reesei GM9414," Enzyme and Microbial Technology, 2007, 40:1087-1094.
Edman et al., "A Protein Sequenator," European J. Biochem., 1967, 1:80-91.
EMBL Database Accession No. DR657362, "EST1047479 FvN Gibberella moniliformis cDNA clone FVNC210, mRNA sequence," Jul. 14, 2005, 2 pages.
European Patent Office Database Accession No. GM007507, "Protease screening methods and proteases identified thereby; Sequence 313 from Patent No. WO2008045148-A1," Nov. 20, 2008, 1 page.
European Patent Office Database Accession No. HC687299, "Methods for producing polypeptides in enzyme-deficient mutants of fusarium venenatum; Sequence 84 from Patent WO2010039840," May 10, 2010, 1 page.
Fabbrini et al., "Comparing the catalytic efficiency of some mediators of lacasse," Journal of Molecular Catalysis B: Enzymatic, Feb. 2002, 16:231-240.
Gasteiger et al., "ExPASy: The proteomics server for in-depth protein knowledge and analysis," Nucleic Acids Research, 2003, 31(13):3784-3788.
Gayle et al., "Identification of Regions in Interleukin-1α Important for Activity," The Journal of Biological Chemistry, 1993, 268(29):22105-22111.
GenBank Accession No. AAA34209 vs, Seq ID No. 10, "alkaline proteinase [Hypocrea lixii], Alignment with Seq ID No. 10 for U.S. Appl. No. 12/803,456," Jan. 3, 2012, 2 pages.
GenBank Accession No. AAA34209 vs, Seq ID No. 10, "alkaline proteinase [Hypocrea lixii], Alignment with Seq ID No. 10 of U.S. Appl. No. 12/803,456," May 28, 1993, 3 pages.
GenBank Accession No. AM294980, "Hypocrea lixii mRNA for serin endopeptidase (p10261 gene)," Apr. 20, 2007, 2 pages.
GenBank Accession No. BI750343, "Fg02_08b01_R Fg02_AAFC_ECORC_Fusarium_graminearum_mycelium Fusarium graminearum cDNA clone Fg02 08b01, mRNA sequence," Jun. 14, 2004, 2 pages.
GenBank Accession No. CAA5806.1, "alkaline protease [Aspergillus fumigatus]" Nov. 14, 2006, 2 pages.

(56) References Cited

OTHER PUBLICATIONS

Geremia et al., "Molecular characterization of the proteinase-encoding gene, prb1, related to mycoparasitism by *Trichoderma harzianum*," Molecular Microbiology, 1993, 8(3):603-613.
Guo et al., "Protein tolerance to random amino acid change," PNAS, 2004, 101(25):9205-9210.
Gurr et al., "The structure and organization of nuclear genes in filamentous fungi," Kinghorn, Jr. (ed.), Gene Structure in Eukaryotic Microbes, IRL Press, Oxford, 1987, pp. 93-139.
Hill et al., "Functional Analysis of conserved Histidines in ADP-Glucose Pyrophosphorylase from *Escherichia coli*," Biochem. Biophys. Res. Comm., 1998, 244:573-577.
International Search Report and Written Opinion issued in International Application No. PCT/EP2012/055762, mailed on Sep. 25, 2012, 12 pages.
International Search Report and Written Opinion issued in International Application No. PCT/EP2011/068837, mailed on Dec. 15, 2011, 13 pages.
Katz et al., "Extreme DNA sequence variation in isolates of *Aspergillus fumigatus*," FEMS Immunology & Medical Microbiology, 1998, 20(4):283-288.
Kelly et al., "Transformation of *Aspergillus niger* by the *amdS* gene of *Aspergillus nidulans*," The EMBO Journal, 1985, 4(2):475-479.
Kredics et al., "Extracellular Proteases of *Trichoderma* Species," Acta Microbiologica et Immunologica Hungarica, 2005, 52(2):169-184.
Laemmli "Cleavage of Structural Proteins during the Assembly of Head of Bacteriophage T4," Nature, Aug. 15, 1970, 227:680-685.
Lazar et al., "Transforming Growth Factor α: Mutation of Aspartic Acid 47 and Leucine 48 Results in Different Biological Activity," Mol. Cell. Biol., 1988, 8(3):1247-1252.
Lewis et al., "Sugar Alcohols (Polyols) in Fungi and Green Plants. I. Distribution, Physiology and Metabolism," New Phytol., 1967, 66:143-184.
Liao et al., "Engineering proteinase K using machine learning and synthetic genes," BMC Biotechnology, 2007, 7(16):1-19.
Manonmani et al. "Purification and properties of an extracellular proteinase of *Trichoderma koningii*," Enzyme Microb. Technol., 1993, 15:624-628.
McDonagh et al., "Production of Caseinophosphopeptides (CPPs) from Sodium Caseinate Using a Range of Commercial Protease Preparations," International Dairy Journal, Mar. 1998, 8(1):39-45.
NCBI Reference Sequence No. XP_383491, "hypothetical protein FG03315.1 [Fusarium graminearum PH-1]," Apr. 9, 2008, 2 pages.
Nielsen et al., "Short Communication—Identification of prokaryotic and eukaryotic signal peptides and prediction of their cleavage sites," Protein Engineering, 1997, 10(1):1-6.
Nielsen et al., "Prediction of signal peptides and signal anchors by a hidden Markov model," Proceedings of the Sixth International Conference on Intelligent Systems for Molecular Biology (ISMB 6), AAAI Press, Menlo Park, California, 1998, pp. 122-130.
Poutanen et al., "Use of matrix-assisted laser desorption/ionization time-of-flight mass mapping and nanospray liquid chromatography/electrospray ionization tandem mass spectrometry sequence tag analysis for high sensitivity identification of yeast proteins separated by two-dimensional gel electrophoresis," Rapid Communications in Mass Spectrometry, 2001, 15(18):1685-1962.
Pozo et al., "Functional analysis of tvsp1, a serine protease-encoding gene in the biocontrol agent *Trichoderma virens*," Fungal Genetics and Biology, Mar. 2004, 41:336-348.
Raeder et al., "Rapid preparation of DNA from filamentous fungi," Letters in Applied Microbiology, 1985, 1:17-20.
Sambrook et al., "Molecular Cloning, a Laboratory Manual," Cold Spring Harbor Laboratory, 3rd ed., New York, US, 2001, p. 6.51, 6.52, 11.27, 6 pages.
Search Report in Finnish Patent Application No. 20106135, dated May 13, 2011, 1 page.
Sharpton et al., "Comparative genomic analyses of the human fungal pathogens *Coccidioides* and their relatives," Genome Research, 2009, 19(10): 1722-1731.
Shevchenko et al., "Mass Spectrometric Sequencing of Proteins from Silver-Stained Polyacrylamide Gels," Anal. Chem., Mar. 1996, 68(5):850-858.
Shimogaki et al., "Purification and Properties of a Novel Surface-Active Agent- and Alkaline-resistant Protease from *Bacillus* sp. Y.," Agric. Biol. Chem., 1991, 55(9):2251-2258.
Siezen et al., "Subtilases: The superfamily of subtilisin-like serine proteases," Protein Science, Mar. 1997, 6(3):501-523.
Stevenson et al., "The Substrate Specificity of Thermomycolase, an Extracellular Serine Proteinase from the Thermophilic Fungus *Malbranchea pulchella* var. *sulfurea*," Biochem. J., 1975, 151(3):527-542.
Steyaert et al., "Co-expression of two genes, a chitinase (*chit42*) and proteinase (*prb1*) implicated in mycoparasitism by *Trichoderma hamatum*," Mycologia, 2004, 96(6):1245-1252.
Suarez et al., "Characterization of genes encoding novel peptidases in the biocontrol fungus *Trichoderma harzianum* CECT 2413 using the TrichoEST functional genomics approach," Curr. Genet., 2007, 51(5):331-342.
Supplementary European Search Report in European Application No. 19870154.2, dated Jul. 22, 2022, 7 pages.
Uniprot Accession No. A4V8W7_TRIHA, "Trichoderma harzianum (Hypocrea lixii)," Alignment with Seq ID No. 18 of U.S. Appl. No. 12/799,638, filed May 29, 2007, 2 pages.
Uniprot Accession No. A5JS74, "Hirsutella minnesotensis," Jun. 26, 2007, 1 page.
Uniprot Accession No. C5PCX1, "*Coccidioides posadasii* (strain C735) (Valley fever fungus), " Sep. 1, 2009, 2 pages.
Uniprot Accession No. C7YXB3, "Fusarium vanettenii (strain ATCC MYA-4622 / CBS 123669 / FGSC 9596 / NRRL 45880 / 77-13-4) (*Fusarium solani* subsp. *pisi*)," Oct. 13, 2009, 1 page.
Uniprot Accession No. C7ZKJ9, "Fusarium vanettenii (strain ATCC MYA-4622 / CBS 123669 / FGSC 9596 / NRRL 45880 / 77-13-4) (*Fusarium solani* subsp. *pisi*)," Oct. 13, 2009, 1 page.
Uniprot Accession No. C9SL49, "Verticillium alfalfae (strain VaMs. 102 / ATCC MYA-4576 / FGSC 10136) (Verticillium wilt of alfalfa) (*Verticillium albo-atrum*)," Nov. 24, 2009, 1 page.
Uniprot Accession No. E3Q3S5, "Colletotrichum graminicola (strain M1.001 / M2 / FGSC 10212) (Maize anthracnose fungus) (*Glomerella graminicola*)," Jan. 11, 2011, 1 page.
Uniprot Accession No. Q03420, "Hypocrea atroviridis (Trichoderma atroviride)," Jun. 16, 2009, 2 pages.
Uniprot Accession No. Q69IF7, "*Phaeosphaeria nodorum* (Glume blotch fungus) (*Parastagonospora nodorum*), " Sep. 13, 2004, 1 page.
Uniprot Accession No. Q86ZV3_TRIHM vs. Seq. ID No. 10, "Trichoderma hamatum—Alignment with Seq ID No. 10 of U.S. Appl. No. 12/803,456," Jun. 1, 2003, 2 pages.
Uniprot Accession No. Q86ZV3_TRIHM vs. SID10, "Trichoderma hamatum—Alignment with Seq ID No. 10 of U.S. Appl. No. 12/803,456," Jan. 3, 2012, 1 page.
Uniprot Accession No. Q86ZV3-TRIHM, "Trichoderma hamatum," Feb. 10, 2009, 1 page.
Uniprot Accession No. Q874K4, "Hypocrea virens (Gliocladium virens) (Trichoderma virens)," Feb. 10, 2009, 1 page.
Venalainen et al., "Evolutionary relationships of the prolyl oligopeptidase family enzymes," European Journal of Biochemistry, 2004, 271:2705-2715.
Whisstock et al., "Prediction of protein function from protein sequence and structure," Quarterly Reviews of Biophysics, 2003, 36(3):307-340.

```
  1   tcatgagcag gcaatcccac tcagttcaat tttgttgatc tacattaatc atgggcgtct
  1                                                              m  g  v 61   tcagcaaact cttgtatctg tcttttgcag tcacggcctc tgtcaatgcc ggtgaaatcc
  4    f  s  k  l  l  y  l  s  f  a  v  t  a  s  v  n  a   g  e  i 121   tttcagtcgc caacaaggac agtgttatcc ctgacacgta tatcgtggtg ttgaaggaag
 24    l  s  v  a  n  k  d  s  v  i  p  d  t  y  i  v  v   l  k  e 181   gagtttcaac ccaggagttc aatgctcata aaaactgggt gaacgagatt catcgcacca
 44    g  v  s  t  q  e  f  n  a  h  k  n  w  v  n  e  i   h  r  t 241   acctcacgag gcgtgacctg ggtttcactg gcgagttaaa gcatagctat gattttggtg
 64    n  l  t  r  r  d  l  g  f  t  g  e  l  k  h  s  y   d  f  g 301   gacatggact gaagggctac agcggcaagt tgatgccac tgccattcag gaaattgcca
 84    g  h  g  l  k  g  y  s  g  k  f  d  a  t  a  i  q   e  i  a 361   atgatcctaa tgtatgcttg ttaagaattc ttcccagcga gatatcttca tgcaagccat
104    n  d  p  n                                Intron 1

421   gcaattgctg acaggtgaat taggtggcct acgtcgaacc ggaccaggag gtgaagcttg
108                                  v  a  y  v  e  p  d   q  e  v  k  l 481   atGCATTGGT GACGCAGAGT AATGCACCAT CCTGGGGCCT TGGCCGTATT TCCAACCGAC
120    d  A  L  V  T  Q  S  N  A  P  S  W  G  L  G  R  I   S  N  R 541   AGGCTGGTAT TCGTGATTAC CACTACGATG ACTCCGCCGG TGAAGGCGTC ATCGTCTATG
140    Q  A  G  I  R  D  Y  H  Y  D  D  S  A  G  E  G  V   I  V  Y 601   ATGTTGACAC CGGTATTGAC ATCAGCCATC CGGATTTCGA GGGCCGTGCT ATATGGGGTT
160    D  V  D  T  G  I  D  I  S  H  P  D  F  E  G  R  A   I  W  G 661   CCAACCATGT CGACCGCGTT AACCAGGATC AGAATGGCCA TGGGACACAC GTTGCTGGTA
180    S  N  H  V  D  R  V  N  Q  D  Q  N  G  H  G  T  H   V  A  G 721   CTATTGGTGG AAGGGCGTAC GGAGTCGCCA AGAAGGCCAC AATAGTGGCT GTCAAGGTTC
200    T  I  G  G  R  A  Y  G  V  A  K  K  A  T  I  V  A   V  K  V 781   TCGACGCCCA GGGGTCAGGT ACTATCAGCG GTATTATTGC TGGTCTTGAC TGGAGTGTCA
220    L  D  A  Q  G  S  G  T  I  S  G  I  I  A  G  L  D   W  S  V 841   ATCATGCTCG ACAGAATGGA GTCACTAGAA GAGCGGCTTT GAACATGAGC CTTGGCGGTG
240    N  H  A  R  Q  N  G  V  T  R  R  A  A  L  N  M  S   L  G  G 901   GGCGCAGTAT CTCTTTCAAT CAGGCTGCTG CAAGTGCTGT CCAAGCCGGA TTGTTCGTCG
260    G  R  S  I  S  F  N  Q  A  A  A  S  A  V  Q  A  G   L  F  V
```

FIG. 1A

```
 961  CGGTTGCTGC CGGAAATGAA GGGgtaagtg acttctttct ggccoctcct atccgtacct
 280    A  V  A   A  G  N   E  G                         Intron 2

1021  gcagaagcta accagattgc tcttattttt tttcttttt caaaatatag CAAAATGCAG
 288                                                        Q  N  A 1081  GTAACACTTC CCCAGCCTCA GAGCCTTCTG TTTGCACAGT AGGGGCAACC TCATCGAATG
 291    G  N  T   S  P  A   S  E  P   S  V  C   T  V  G  A  T  S  S  N 1141  ATGCCGCCAC ATCCTGGTCC AACTATGGCT CAGTTGgtac gtagggctcg gttttattta
 311    D  A  A   T  S  W   S  N  Y   G  S  V 1201  ttacttcttc cccacatgcg atcagaccgg ccgctgacta tatttagTTG ACGTTTACGC
 323                              Intron 3                   V  D  V  Y 1261  TCCCGGAGAC GCAATTGTCT CTACCTGGCC CGGTGGCGGT TCCAGGTCTC TCTCAGGCAC
 327    A  P  G  D   A  I  V  S  T  W   P  G  G   S  R  S   L  S  G 1321  ATCGATGGCT TCTCCACACG TCGCCGGCCT GGGTGCATAC CTCATCGCTC TGGAGGGCAT
 347    T  S  M  A   S  P  H  V  A  G   L  G  A  Y  L  I  A  L  E  G 1381  TAGCGGAGGC AGTGTATGTG ACCGTATCAA AGAGCTGGCT CAACCTGTCG TCCAGCCTGG
 367    I  S  G  G   S  V  C   D  R  I   K  E  L  A   Q  P  V  Q  P 1441  TCCAGGCACC ACCAACCGTC TTATCTACAA CGGCAGTGGC CGCtaaattg atagtagcta
 387    G  P  G  T   T  N  R   L  I  Y   N  G  S  G   R  *

1501  cagaaggcat agggcttgcg gcgactcggg caatgcagga tatttt
```

FIG. 1B

PROTEASE ENZYME VARIANTS AND USES THEREOF

CROSS REFERENCE TO RELATED APPLICATIONS

This application is a U.S. National Phase Application under 35 U.S.C. § 371 of International Application PCT/FI2019/050724, filed on Oct. 10, 2019, which claims the benefit of European Application No. 18200114.9, filed on Oct. 12, 2018, the entire contents of both of which are hereby incorporated by reference in their entireties.

SEQUENCE LISTING

This application contains a Sequence Listing that has been submitted electronically as an ASCII text file named "UpdatedSequenceListing_ST25.txt." The ASCII text file, created on May 30, 2024, is 27,352 bytes in size. The material in the ASCII text file is hereby incorporated by reference in its entirety.

FIELD OF THE INVENTION

The present invention relates to variants of a serine protease enzyme, particularly to variants of a fungal serine protease enzyme useful in various applications, particularly in detergents. The invention further relates to nucleic acid molecules encoding said enzyme variants, recombinant vectors, a host cell for producing said enzyme variants, enzyme compositions comprising said enzyme variants as well as processes for preparing such compositions. This invention relates also to various uses of said enzyme variants and compositions comprising said enzyme variants.

BACKGROUND

Microbial proteases are among the most important hydrolytic enzymes and find applications in various industrial sectors, such as detergents, food, leather, pharmaceuticals, diagnostics, waste management and silver recovery. Microbial extracellular proteases account for a major part of the total worldwide industrial enzyme sales (Cherry and Fidantsef, 2003). Approximately 90% of the commercial proteases are detergent enzymes (Gupta et al., 2002). The commercial detergent preparations currently in use comprise the naturally occurring alkaline serine proteases (EC 3.4.21) of the subtilisin family or subtilisins (EC 3.4.21.62), originating from *Bacillus* species, or are recombinant protease preparations thereof (Maurer, 2004).

Examples of commercial proteases are such as Subtilisin Carlsberg (Alcalase®), Subtilisin 309 (Savinase®), Subtilisin 147 (Esperase®), Kannase®, Everlase®, Ovozyme®, and the cold-wash protease Polarzyme® (Novozymes A/S, DK), Purafect®, Purafect® Ox, Purafect® Prime and Properase® (Genencor Int., Inc., USA), and the BLAP S and X series (Henkel, DE).

The major problem in the use of proteases in liquid detergents is their instability and proteolytic activity against other enzymes in the detergents. In liquid detergents enzymes are in direct contact with water and chaotropic agents like anionic surfactants and complexing agents, which can lead to irreversible denaturation. Proteases degrade proteins including themselves and other enzymes in detergent formulations. The auto-proteolysis is enhanced by surfactants and heat. Thus, the stability of enzymes in liquid detergents containing protease represents a major challenge for product development (Maurer, 2010). Various methods have been used for improving the stability of industrial serine proteases. Based on the information derived from the crystal structures and sequence similarity comparisons between homologous proteins, variants with improved stability and/or improved performance may be designed. Variants of the natural serine proteases with improved catalytic efficiency and/or better stability towards temperature, oxidizing agents and different washing conditions, as well as improved storage stability in liquid detergents have been developed through site-directed and/or random mutagenesis. Proteases are deliberately or randomly modified by methods known from the prior art and are optimized for example for use in detergents and cleaning agents. These include point mutagenesis, deletion or insertion mutagenesis, or fusion with other proteins or protein parts. Optimized variants for some proteases are known from the prior art. Optimized variants are known particularly of subtilisin enzyme. For example, application WO199523221 describes, among other mutants, a mutation in a subtilisin of *Bacillus lentus* DSM 5483, applications WO2011032988, WO2011141358, WO2012080201 and WO2012080202 describe improved protease performance as well as reduced damage of the protease and other molecules when using such a mutation, based on a subtilisin of *Bacillus lentus* DSM 5483.

Thermomycolin EC 3.4.21.65, isolated as an extracellular alkaline endopeptidase, is produced by a thermophilic fungus *Malbranchea pulcella* var. *sulfurea*. Thermomycolin is described as a 325 residue, single-chain protein. It has the active-site sequence -Leu-Ser-(Gly)-Thr-Ser*-Met-, which is typical for a member of the subtilisin family. Thermomycolin possesses one disulfide bridge, which is exceptional. Thermomycolin is not as thermostable as the extracellular serine proteinases of thermophilic bacteria, but it is more stable than most fungal proteinases (Gaucher and Stevenson, 2004). According to Ong and Gaucher (1975) the thermal inactivation of Thermomycolin occurs at 73° C. in the presence of 10 mM Ca'. Thermomycolin hydrolyses casein on broad pH range. The optimum pH for hydrolysis of casein is about 8.5. EP2691520B1 (AB Enzymes Oy) discloses a Thermomycolin protease of *Malbranchea cinnamomea* (Lib.) Oorschot de Hoog ALKO4122, which has improved stability and improved wash performance and stain removal properties when compared to commercial protease products Savinase 16L and Savinase Ultra 16L.

Despite the fact that numerous patent publications, reviews and articles have been published, disclosing serine proteases from various microorganisms, there is still a great need for new proteases, which are suitable for and effective in modifying, degrading and removing proteinaceous materials of different stains and which are stable in the presence of detergents with highly varying properties. Due to the autocatalytic property of serine proteases, the stability during storage is also very important. However, it is important that also the other enzymes in detergents are stable in the presence of protease. Protease inhibitors could potentially be used to stabilize proteases in compositions comprising serine proteases. However, the inhibitors do not always work optimally and therefore, there is especially great need for new proteases which are efficient in stain removal but are less aggressive towards themselves and other enzymes.

It is also desirable that the serine protease can be produced in high amounts, and can be cost-effectively down-stream processed, by easy separation from cells or mycelia.

SUMMARY OF THE INVENTION

The object of the present invention is to provide novel *Malbranchea* protease variants which are active at broad pH ranges and function well at broad temperature ranges. The serine proteases for detergent application must be stable also in the presence of detergents and to be compatible with detergents. Further objects of the invention are to provide nucleic acid molecules encoding said enzyme variants, recombinant vectors, a host cell for producing said enzyme variants, compositions comprising said enzyme variants, a process for preparing such compositions, as well as uses of said enzyme variants and compositions comprising said enzyme variants.

The object of the present invention is to provide novel *Malbranchea* protease variants that are less aggressive towards other enzymes when stored or used in combination with these variants and also have better performance in stain removal as compared to the wild type *Malbranchea* protease, while the stability of the enzyme variants is as good as that of wild type *Malbranchea* protease.

The fungal serine protease according to the invention can be produced in high-yielding fungal hosts and its downstream processing, e.g. separation of fermentation broth and mycelia is easy to perform.

The present invention relates to a fungal serine protease enzyme variant, which has serine protease activity and comprises an amino acid sequence having at least 70% identity to the amino acid sequence as defined in SEQ ID NO: 2 and which comprises the amino acid D at position 103 and/or the amino acid E at position 105 in the numbering according to SEQ ID NO: 2. A preferred serine protease is a mutant serine protease that is a derivative of the *Malbranchea cinnamomea* (Lib.) Oorschot de Hoog wild type protease.

The present inventors found that stain removal performance of the fungal serine protease variants that mean here the same as recombinant serine protease enzymes from *Malbranchea* in varying test conditions, on different stains, measured as deltaL* is better than the performance of wild type *Malbranchea* protease enzyme.

An object of the invention is a recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2.

Another object of the invention is an isolated nucleic acid molecule comprising a polynucleotide sequence which encodes a serine protease enzyme selected from the group consisting of: (a) a nucleic acid molecule encoding a polypeptide having serine protease activity and comprising the amino acid sequence as depicted in SEQ ID NO: 4 or SEQ ID NO: 6 or SEQ ID NO: 8; and (b) a nucleic acid molecule comprising the coding sequence of the nucleotide sequence as depicted in SEQ ID NO: 3 or SEQ ID NO: 5 or SEQ ID NO: 7.

Still a further object of the present invention is a recombinant expression vector comprising the isolated nucleic acid according to claim 4 operably linked to regulatory sequences capable of directing expression and secretion of said serine protease enzyme in a suitable host.

A host cell comprising the recombinant expression vector and an enzyme preparation, which comprises the recombinant serine protease enzyme according to the invention are also disclosed.

One object of the invention is a process for producing a protease enzyme, the method comprising the step of introducing an amino acid substitution Q103D and/or S105E into the sequence which comprises an amino acid sequence having at least 70% identity to the amino acid sequence as defined in SEQ ID NO: 2.

Use of the recombinant serine protease enzyme or the enzyme preparation according to the present invention for detergents, for treating fibers, for treating proteinaceous materials, for treating food or feed, or for applications involving modification, degradation or removal of proteinaceous material is also an aspect of this invention.

According to the present invention the recombinant serine protease enzyme or the enzyme preparation can be used as a detergent additive. According to the present invention the recombinant serine protease enzyme or the enzyme preparation can be used in liquid detergent or a solid detergent preferably in a form of a bar, a homogenous tablet, a tablet having two or more layers, a pouch having one or more compartments, a regular or compact powder, a granule, a granulate, a paste, a gel, or a regular, compact or concentrated liquid. Also a detergent composition that comprises surfactants, the recombinant serine protease enzyme or the enzyme preparation according to the present invention, and additives selected from the group consisting of stabilizers, buffers, builders, bleaching agents, mediators, anti-corrosion agents, antiredeposition agents, caustics, abrasives, optical brighteners, dyes, perfumes, pigments, and preservatives, is one aspect of the present invention.

BRIEF DESCRIPTION OF DRAWINGS

FIGS. 1A and B shows the nucleotide sequence of the *Malbranchea* ALKO4122 protease gene, its partial promoter (50 nucleotides upstream from ATG) and terminator sequences (60 nucleotides downstream from the stop codon) (SEQ ID NO:11) and the deduced amino acid sequence of the encoded protease (SEQ ID NO:12). The putative signal peptide analyzed by SignalP V3.0 program is in lower case letters and underlined. The pro sequence and the deduced amino acids of the pro sequence are in lower case letters. The mature nucleotide and peptide sequences are in capital letters. The three putative intron sequences are in lower case, italic letters and marked by a dotted line below the nucleotide sequence. The stop codon is shown by an asterisk below the sequence. The mutated amino acids Q103 and S105 are bolded.

SEQUENCE LISTING

Figure 2:
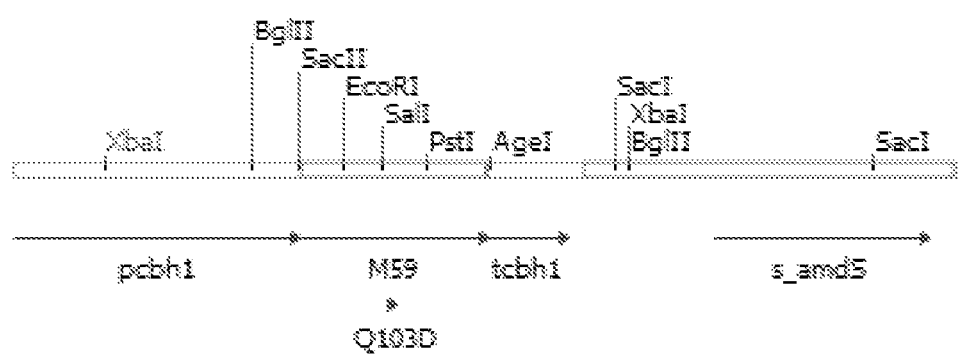
FIG. 2 schematically shows the expression cassette pALK4521 used for production of M59 *Malbranchea* protease variant in *Trichoderma reesei*. The 7234 bp expression cassette was cleaved from the plasmid vector backbones using NotI restriction enzyme. pcbh1, cbh1 promoter; tcbh1, cbh1 terminator; s_amdS, synthetic gene encoding *Aspergillus nidulans* asetamidase (selection marker); M59, a variant *Malbranchea* protease gene. The mutation in the mature amino acid sequence of the variant protease compared to the wild type mature sequence is shown below the name of the variant gene. The synthetic amdS gene is expressed from the native *A. nidulans* amdS promoter. The expression cassettes pALK4522 and pALK4523 for production of M60 and M61 variants, respectively, were similar in their structure as pALK4521 for production of M59 and shown in the figure.

SEQ ID NO: 1 The nucleotide sequence encoding the amino acid sequence of mature *Malbranchea* ALKO4122 protease. The full-length gene is included in the plasmid pALK3094 as described in EP2691520B1.

SEQ ID NO: 2 The amino acid sequence of mature *Malbranchea* ALKO4122 protease including amino acids Ala121 to Arg401 of the protease.

SEQ ID NO: 3 The nucleotide sequence encoding the amino acid sequence of mature *Malbranchea* ALKO4122 protease with mutation CAG→GAC or CAG→GAT at position 307-309 resulting to mutation Q103 D in the mature protease sequence.

SEQ ID NO: 4 The amino acid sequence of the M59 derivative of mature *Malbranchea* ALKO4122 protease including amino acids Ala121 to Arg401 of the mature protease and mutation Q103D at position 103 of the mature protease.

SEQ ID NO: 5 The nucleotide sequence encoding the amino acid sequence of mature *Malbranchea* ALKO4122 protease with mutation TCA→GAG or TCA→GAA at position 313-315 resulting to mutation S105E in the mature protease sequence.

SEQ ID NO: 6 The amino acid sequence of the M60 derivative of mature *Malbranchea* ALKO4122 protease including amino acids Ala121 to Arg401 of the protease and mutation S105E at position 105 of the mature protease.

SEQ ID NO: 7 The nucleotide sequence encoding the amino acid sequence of mature *Malbranchea* ALKO4122 protease with mutations CAG→GAC and TCA→GAT at positions 307-309 and 313-315, respectively.

SEQ ID NO: 8 The amino acid sequence of the M61 derivative of mature *Malbranchea* ALKO4122 protease including amino acids Ala121 to Arg401 of the protease and mutations Q103D and S105E at positions 103 and 105, respectively, of the mature protease.

SEQ ID NO: 9 The nucleotide sequence encoding the amino acid sequence of the full-length *Malbranchea* ALKO4122 protease.

SEQ ID NO: 10 The amino acid sequence of the full-length *Malbranchea* ALKO4122 protease (includes the signal sequence, pro-sequence and sequence of the mature form).

DETAILED DESCRIPTION

The present invention provides novel serine protease enzyme variants of fungal origin.

In the present context, "derived from" is intended not only to indicate a serine protease produced or producible by a strain of the organism in question, but also a serine protease encoded by a DNA sequence isolated from such strain and produced in a host organism transformed with said DNA sequence. Finally, the term is intended to indicate a serine protease, which is encoded by a DNA sequence of synthetic and/or cDNA origin and which has the identifying characteristics of serine protease in question.

The fungal serine protease enzyme variants of the invention are based on *Malbranchea* protease, preferably on *Malbranchea cinnamomea* (Lib.) Oorschot de Hoog (Synonym of *Malbranchea pulchella* var. *sulfurea* (Miehe) Cooney & R. Emers) protease. The full-length fungal serine protease enzyme, wherein the variants of the invention are based on, is encoded by the polynucleotide sequence included in pALK3094 deposited in *Escherichia coli* RF8791 under accession number DSM 24410, as disclosed in the patent EP2691520 B1 (AB Enzymes Oy).

Preferably the invention relates to fungal serine protease enzyme variants, which have serine protease activity and comprise an amino acid sequence of the mature protease as defined in SEQ ID NO: 4 (M59) or the amino acid sequence of the mature protease as defined in SEQ ID NO: 6 (M60) or the amino acid sequence of the mature protease as defined in SEQ ID NO:8 (M61).

The fungal serine protease enzyme variant of the present disclosure is produced from recombinant expression vector comprising the nucleic acid molecule encoding a fungal serine protease variant of the invention, operably linked to regulatory sequences capable of directing the expression of the serine protease enzyme in a suitable host. Non-limiting examples of a host cell are fungal cells, filamentous fungal cells from Division Ascomycota, Subdivision Pezizomycotina; preferably from the group consisting of members of the Class Sordariomycetes, Subclass Hypocreomycetidae, Orders Hypocreales and Microascales and *Aspergillus*,

*Chrysosporium, Myceliophthora* and *Humicola*; more preferably from the group consisting of Families Hypocreacea, Nectriaceae, Clavicipitaceae, Microascaceae, and Genera *Trichoderma* (anamorph of *Hypocrea*), *Fusarium, Gibberella, Nectria, Stachybotrys, Claviceps, Metarhizium, Villosiclava, Ophiocordyceps, Cephalosporium*, and *Scedosporium*; more preferably from the group consisting of *Trichoderma reesei* (*Hypocrea jecorina*), *T. citrinoviridae, T longibrachiatum, T. virens, T. harzianum, T. asperellum, T. atroviridae, T. parareesei, Fusarium oxysporum, F. gramineanum, F. pseudograminearum, F. venenatum, Gibberella fujikuroi, G. moniliformis, G. zeaea, Nectria* (*Haematonectria*) *haematococca, Stachybotrys chartarum, S. chlorohalonata, Claviceps purpurea, Metarhizium acridum, M. anisopliae, Villosiclava virens, Ophiocordyceps sinensis, Acremonium* (*Cephalosporium*) *chrysogenum*, and *Scedosporium apiospermum*, and *Aspergillus niger, Aspergillus awamori, Aspergillus oryzae, Chrysosporium lucknowense, Myceliophthora thermophila, Humicola insolens*, and *Humicola grisea*, most preferably *Trichoderma reesei*. Non-limiting examples of a host cell are yeasts (e.g. *Saccharomyces cerevisiae, Pichia pastoris, Yarrowia lipolytica*) and bacterial cells, preferably gram positive Bacilli (e.g. *Bacillus subtilis, B. licheniformis, B. megaterium, B. amyloliquefaciens, B. pumilus*), gram-negative bacteria (e.g. *Escherichia coli*) and actinomycetales (e.g. *Streptomyces* sp.).

In an embodiment the host cell is a fungal cell, preferably a filamentous fungal cell, such as *Aspergillus, Trichoderma* or *Trichoderma reesei*. In an embodiment the host cell is a bacterial cell, preferably a gram-positive *Bacillus* cell, such as *B. subtilis, B. licheniformis, B. megaterium, B. amyloliquefaciens* or *B. pumilus*.

Preferably, said enzyme variant is produced in *Trichoderma* or *Aspergillus*, most preferably in *T. reesei*.

The present invention relates also to an isolated nucleic acid molecule comprising a polynucleotide sequence encoding a serine protease enzyme variant selected from the group consisting of:
  (a) a nucleic acid molecule encoding a polypeptide having serine protease activity and comprising the amino acid sequence as depicted in SEQ ID NO: 4;
  (b) a nucleic acid molecule encoding a polypeptide having serine protease activity and comprising the amino acid sequence as depicted in SEQ ID NO: 6;
  (c) a nucleic acid molecule encoding a polypeptide having serine protease activity and comprising the amino acid sequence as depicted in SEQ ID NO: 8;
  (d) a nucleic acid molecule comprising the coding sequence of the nucleotide sequence as depicted in SEQ ID NO: 3;
  (d) a nucleic acid molecule comprising the coding sequence of the nucleotide sequence as depicted in SEQ ID NO: 5; and
  (d) a nucleic acid molecule comprising the coding sequence of the nucleotide sequence as depicted in SEQ ID NO: 7.

The present invention relates to a process of producing a polypeptide having serine protease activity, said process comprising the steps of culturing the host cell of the invention and recovering the polypeptide. Also, within the invention is a polypeptide having serine protease activity encoded by the nucleic acid sequence of the invention and which is obtainable by the process described above.

The invention relates to a process for obtaining an enzyme preparation comprising the steps of culturing a host cell of the invention and either recovering the polypeptide from the cells or separating the cells from the culture medium and obtaining the supernatant. Within the invention is also an enzyme preparation obtainable by the process described above.

The invention relates to an enzyme preparation, which comprises the serine protease enzyme variant or variants of the invention.

The term "mutant" or "variant" also is used herein in reference to a serine protease enzyme that contains a mutation with respect to a corresponding wild type serine protease enzyme.

The invention further relates to a composition comprising the serine protease enzyme variant or variants of the invention.

The enzyme preparation or composition (e.g. detergent formulation) containing the protease enzyme variant or variants of the invention may further comprise other enzymes selected from the group consisting of proteases (other protease than that of the invention), amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, laccases and/or peroxidases and oxidases with or without a mediator as well as suitable additives selected from the group consisting of stabilizers, buffers, surfactants, bleaching agents, mediators, anti-corrosion agents, builders, anti-redeposition agents, optical brighteners, dyes, pigments, perfumes, caustics, abrasives and preservatives, etc.

The spent culture medium of the production host can be used as such, or the host cells may be removed, and/or it may be concentrated, filtrated or fractionated. It may also be dried. The enzyme preparation and the composition comprising the serine protease enzyme of the invention may be in the form of liquid composition or a solid composition such as solution, dispersion, paste, powder, granule, granulate, coated granulate, tablet, cake, crystal, crystal slurry, gel or pellet. The enzyme may be in immobilized form in the preparation or in the composition.

Also within the invention is the use of the serine protease enzyme variant or variants or the enzyme preparation of the invention for detergents, for treating fibers, for treating proteinaceous material such as wool, hair, leather, silk, for treating food or feed, or for any applications involving modification, degradation or removal of proteinaceous material. The enzyme composition is used in textile and detergent industry, biomass processing and biomass hydrolysis, preferably in biofuel, starch, pulp and paper, food, baking, feed or beverage industries. Particularly, the enzyme or enzyme preparation is useful as a detergent additive in liquid detergent or a solid detergent preferably in a form of a bar, a homogenous tablet, a tablet having two or more layers, a pouch having one or more compartments, a regular or compact powder, a granule, a granulate, a paste, a gel, or a regular, compact or concentrated liquid.

These enzyme variants are active at broad pH and temperature ranges in washing, and particularly good performance at low temperature ranges as well as at moderate and high temperatures. The enzyme variants are ideal for detergent applications, withstanding typical detergent compositions and being effective at low enzyme levels in detergent solutions. Particularly, the protease variants are active at application temperatures 0° C.-90° C., the preferred range being from 5° C. to 60° C. Each of the fungal serine protease enzyme variants of the invention is capable in degrading or removing proteinaceous stains in the presence of detergents at a temperature from 0° C. to 90° C., preferably at a temperature from 5° C. to 60° C. The fungal serine protease variants of the invention, depending on the washing conditions and auxiliary ingredients and additives in detergents, are useful particularly in temperatures at or below 60° C.

The protease of the invention is also highly stable in liquid detergent compositions. Thus, the present invention provides novel serine protease variants for use in detergent and other applications, particularly in liquid formulations. The fungal serine protease variants can be produced in high-yielding fungal hosts and their down-stream processing, e.g. separation of fermentation broth and mycelia is easy to perform.

By "serine protease" or "serine endopeptidase" or "serine endoproteinase" is in connection to this invention meant an enzyme classified as EC 3.4.21 by the Nomenclature of the International Union of Biochemistry and Molecular Biology. Proteases can be classified using group specific inhibitors. The diverse group of serine protease inhibitors includes synthetic chemical inhibitors and natural proteinaceous inhibitors. Thus, the serine protease activity can be determined in an assay based on cleavage of a specific substrate or in an assay using any protein containing substrate with or without a specific inhibitor of serine proteases under suitable conditions.

By the term "serine protease activity" as used in the invention is meant hydrolytic activity on protein containing substrates, e.g. casein, haemoglobin and BSA. The methods for analysing proteolytic activity are well-known in the literature and are referred e.g. in Gupta et al. (2002).

The serine proteases are synthesized as inactive zymogenic precursors or zymogens in the form of a pre-proenzyme, which are activated by removal of the signal sequence (secretion signal peptide or prepeptide) and the prosequence (propeptide) to yield an active mature form of the enzyme (Chen and Inouye, 2008).

Examples of suitable signal sequences are those of the fungal or yeast organisms. Such signal sequences are well known from the literature. Suitable prosequences are those of fungal or yeast or bacterial proteases.

The recombinant vector may further comprise sequences facilitating integration of the vector into the host chromosomal DNA to obtain stable expression and/or to facilitate targeting to a certain position in the host genome.

The term "mature" means the form of the serine protease enzyme which after removal of the signal sequence (prepeptide) and propeptide comprises the essential amino acids for enzymatic or catalytic activity. In filamentous fungi it is the native form secreted into the culture medium. The first amino acid of mature sequence can be determined by N-terminal sequencing of secreted protease. In case no biochemical data is available the location of the N-terminus can be estimated by aligning the amino acid sequence with mature amino acid sequence(s) of homologous protein(s). The alignment can be performed using e.g. ClustalW2 alignment (http://www.ebi.ac.uk/Tools/msa/clustalw2/).

To improve the performance of the *Malbranchea* serine protease in varying industrial applications, such as in detergents, it is desirable to improve the properties of the native enzyme. These properties include e.g. storage stability, stability in the presence or absence of detergent, pH stability, oxidative stability or resistance against bleaching agents and substrate specificity. The autoproteolytic activity of the enzyme has an effect on the storage stability and it should be as low as possible. It is also self-evident that for example in laundry and dish washing compositions the wash performance of the modified protease should not be impaired in comparison to the parent or precursor protease enzyme. In other words, it is desirable that the enzyme variants have similar or even improved wash performance and stain removal properties when compared to the parent serine protease.

The produced serine protease variants can be purified by using conventional methods of enzyme chemistry, such as salt preparation, ultrafiltration, ion exchange chromatography, affinity chromatography, gel filtration and hydrophobic interaction chromatography. Purification can be monitored by protein determination, enzyme activity assays and by SDS polyacrylamide gel electrophoresis. The enzyme activity and stability of the purified enzyme at various temperature and pH values as well as the molecular mass and the isoelectric point can be determined.

Protease activity is generally based on degradation of soluble substrates. In detergent application proteases have to work on substances which are at least partly insoluble. Thus, an important parameter for a detergent protease is the ability to adsorb to and hydrolyse these insoluble fragments.

In the presence of a detergent, the fungal serine protease variants of the invention function at temperatures as defined above and particularly, said fungal serine protease variants have a good performance in the presence of detergent. Stain removal performance of the fungal serine protease variants from *Malbranchea* in varying test conditions, on different stains, measured as deltaL* is better than the performance of wild type *Malbranchea* protease enzyme.

According to a preferred embodiment of the invention each of the recombinant fungal serine protease enzyme variants is a polypeptide having serine protease activity and comprising an amino acid sequence having at least 70% identity to the amino acid sequence of the mature *Malbranchea* ALKO4122 protease as defined in SEQ ID NO: 2 and comprising amino acid substitution at position 103 or at position 105 or at positions 103 and 105. According to the more preferred embodiment the substitution at position 103 is Q103D and at position 105 is S105E.

According to a preferred embodiment of the invention a recombinant serine protease enzyme comprises an amino acid sequence having at least 70% identity to an amino acid sequence as defined in SEQ ID NO: 2 and comprises amino acid D at position 103 and/or amino acid E at position 105 in the numbering according to SEQ ID NO: 2. Preferably said recombinant serine protease enzyme has improved stain removal performance.

According to a preferred embodiment of the invention a recombinant serine protease enzyme comprises an amino acid sequence having at least 70% identity to an amino acid sequence as defined in SEQ ID NO: 2 and comprises amino acid D at position 103 in the numbering according to SEQ ID NO: 2 and has improved stain removal performance.

According to a preferred embodiment of the invention a recombinant serine protease enzyme comprises an amino acid sequence having at least 70% identity to an amino acid sequence as defined in SEQ ID NO: 2 and comprises amino acid E at position 105 in the numbering according to SEQ ID NO: 2 and has improved stain removal performance.

Preferably, the protease enzyme variant polypeptide comprises an amino acid sequence having at least about 70% and increasingly preferably to an extent of at least about 75%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5% and about 99% identity to the amino acid sequence of the mature *Malbranchea* ALKO4122 protease as defined in SEQ ID NO: 2.

According to a preferred embodiment of the invention a recombinant serine protease enzyme comprises an amino acid sequence having at least 82% identity to an amino acid sequence as defined in SEQ ID NO: 2 and comprises amino acid D at position 103 and/or amino acid E at position 105 in the numbering according to SEQ ID NO: 2. Preferably, said recombinant serine protease enzyme has improved stain removal performance.

According to a preferred embodiment of the invention a recombinant serine protease enzyme comprises an amino acid sequence having at least 82% identity to an amino acid sequence as defined in SEQ ID NO: 2 and comprises amino acid D at position 103 in the numbering according to SEQ ID NO: 2 and has improved stain removal performance.

According to a preferred embodiment of the invention a recombinant serine protease enzyme comprises an amino acid sequence having at least 82% identity to an amino acid sequence as defined in SEQ ID NO: 2 and comprises amino acid E at position 105 in the numbering according to SEQ ID NO: 2 and has improved stain removal performance.

By the term "identity" is here meant the identity between two amino acid sequences compared to each other within the corresponding sequence region having approximately the same amount of amino acids. For example, the identity of a mature sequence of the two amino acid sequences may be compared. The amino acid sequences of the two molecules to be compared may differ in one or more positions, which however does not alter the biological function or structure of the molecules. Such variation may occur naturally in different organisms or due to mutations in the amino acid sequence or they may be achieved by specific mutagenesis. The variation may result from deletion, substitution or insertion of one or more positions in the amino acid sequence. The identity of the sequences is measured by using ClustalW2 alignment (http://www.ebi.ac.uk/Tools/msa/clustalw2/) with default settings (Protein Weight Matrix: Gonnet, Gap open: 10, Gap extension: 0.20, Gap distances 5).

The serine protease, suitably the fungal serine protease of the invention has "good performance in the presence of detergent", i.e. is capable of degrading or removing proteinaceous stains or material in the presence of detergent at wide temperature ranges, specifically at lower temperature ranges than the present commercial subtilisin products. In the presence of a detergent the enzyme of the invention functions well between 5° C. and 60° C.

One preferred embodiment of the invention is the fungal serine protease enzyme encoded by an isolated nucleic acid molecule, which comprises the nucleotide sequence SEQ ID NO: 3, SEQ ID NO: 5 or SEQ ID NO: 7.

One embodiment of the invention is the serine protease enzyme produced from a recombinant expression vector comprising the nucleic acid molecule, which encodes the fungal serine protease enzyme variant as characterized above operably linked to regulatory sequences capable of directing the expression and secretion of said serine protease enzyme in a suitable host. Construction of said recombinant expression vector and use of said vector is described in more detail in EP2691520B1.

The present invention relates also to an isolated nucleic acid molecule comprising a polynucleotide sequence encoding the serine protease enzyme variant selected from the group consisting of:

(a) a nucleic acid molecule encoding a polypeptide having serine protease activity and comprising the amino acid sequence as depicted in SEQ ID NO: 4, SEQ ID NO: 6 or SEQ ID NO: 8; and (b) a nucleotide sequence encoding the amino acid sequence of mature *Malbranchea* ALKO4122 protease with mutations CAG→GAC or GAT and/or TCA→GAG or GAA (at position(s) 307-309 and/or 313-315) as depicted in SEQ ID NO: 3, SEQ ID NO: 5 or SEQ ID NO: 7.

The nucleic acid molecule of the invention may be DNA or RNA, wherein the DNA may constitute of the genomic DNA or cDNA or synthetic DNA. RNA may constitute of natural RNA or synthetic RNA.

Thus, within the scope of the invention is an isolated polynucleotide sequence or isolated nucleic acid molecule, which encodes a fungal serine protease enzyme variant or polypeptide comprising the amino acid sequence of the mature form of the *Malbranchea* ALKO4122 enzyme characterized in SEQ ID NO: 2 with amino acid substitution at position 103 and/or at position 105.

The present invention relates also to a recombinant expression vector or recombinant expression construct, which can be used to propagate or express the nucleic acid sequence encoding the chosen serine protease variant in a suitable prokaryotic or eukaryotic host. The recombinant expression vector comprises DNA or nucleic acid sequences which facilitate or direct expression and secretion of the serine protease encoding sequence in a suitable host, such as promoters, enhancers, terminators (including transcription and translation termination signals) and signal and pro sequences operably linked the polynucleotide sequence encoding said serine protease. The expression vector may further comprise marker genes for selection of the transformant strains or the selection marker may be introduced to the host in another vector construct by co-transformation. Said regulatory sequences may be homologous or heterologous to the production organism or they may originate from the organism, from which the gene encoding the serine protease is isolated.

Examples of promoters for expressing the serine protease of the invention in filamentous fungal hosts are the promoters of *Trichoderma reesei* native proteins, e.g. cellobiohydrolase 1, *A. oryzae* TAKA amylase, alkaline protease ALP and triose phosphate isomerase, *Rhizopus miehei* lipase, *Aspergillus niger* or *A. awamori* glucoamylase (glaA), *Fusarium oxysporum* trypsin-like protease and *Chrysosporium lucknowense* cellobiohydrolase 1 promoter.

In yeast, for example promoters of *S. cerevisiae* enolase (ENO-1), galactokinase (GAL1), alcohol dehydrogenase (ADH2) and 3-phosphoglycerate kinase can be used to provide expression.

Examples of promoter sequences for directing the transcription of the serine protease of the invention in a bacterial host are the promoter of lac operon of *Escherichia coli*, the *Streptomyces coelicolor* agarase dagA promoter, the promoter of the *B. licheniformis* alpha-amylase gene (amyL), the promoter of the *B. stearothermophilus* maltogenic amylase gene (amyM), the promoters of the *B. subtilis* xylA and xylB genes, etc.

Suitable terminators include those of the above-mentioned genes or any other characterized terminator sequences.

Suitable transformation or selection markers include those which give a selectable property to the transformant, for example the *Aspergillus* amdS or complement a defect in the host, for example the *Aspergillus* niaD or dal genes from

*B. subtilis* or *B. licheniformis*. The selection may be based also on a marker conferring antibiotic resistance, such as ampicillin, kanamycin, chloramphenicol, tetracycline, phleomycin or hygromycin resistance.

The present invention relates also to host cells comprising the recombinant expression vector as described above. Suitable hosts for production of the fungal serine protease enzyme are homologous or heterologous hosts, such as the microbial hosts including fungi, yeasts and bacteria. Production systems in plant or mammalian cells are also possible.

Suitable expression and production host systems are for example the production system developed for the filamentous fungus host consisting of members of the Class Sordariomycetes, Subclass Hypocreomycetidae, Orders Hypocreales and Microascales and *Aspergillus, Chrysosporium, Mycehophthora* and *Humicola*; more preferably from the group consisting of Families Hypocreacea, Nectriaceae, Clavicipitaceae, Microascaceae, and Genera *Trichoderma* (anamorph of *Hypocrea*), *Fusarium, Gibberella, Nectria, Stachybotrys, Claviceps, Metarhizium, Villosiclava, Ophiocordyceps, Cephalosporium*, and *Scedosporium*; more preferably from the group consisting of *Trichoderma reesei* (*Hypocrea jecorina*), *T. citrinoviridae, T longibrachiatum, T. virens, T harzianum, T. asperellum, T. atroviridae, T. parareesei, Fusarium oxysporum, F. gramineanum, F. pseudogramineanum, F. venenatum, Gibberella fujikuroi, G. moniliformis, G. zeaea, Nectria (Haematonectria) haematococca, Stachybotrys chartarum, S. chlorohalonata, Claviceps purpurea, Metarhizium acridum, M anisopliae, Villosiclava virens, Ophiocordyceps sinensis, Acremonium (Cephalosporium) chrysogenum*, and *Scedosporium apiospermum*, and *Aspergillus niger, Aspergillus awamori, Aspergillus oryzae, Chrysosporium lucknowense, Myceliophthora thermophila, Humicola insolens*, and *Humicola grisea*, most preferably *Trichoderma reesei*. Non-limiting examples of a production system are yeasts (e.g. *Saccharomyces cerevisiae, Pichia pastoris, Yarrowia lipolytica*) and bacteria, preferably gram-positive Bacilli (e.g. *Bacillus subtilis, B. licheniformis, B. megaterium, B. amyloliquefaciens, B. pumilus*), gram-negative bacteria (e.g. *Escherichia coli*) and actinomycetales (e.g. *Streptomyces* sp.).

The present invention relates also to a process for producing a polypeptide having serine protease activity, said process comprising the steps of culturing the natural or recombinant host cell carrying the recombinant expression vector for a serine protease variant of the invention under suitable conditions and optionally isolating said enzyme. The production medium is a medium suitable for growing the host organism and may contain inducers for efficient expression. Suitable media are well-known from the literature.

The invention relates to a polypeptide having serine protease activity, said polypeptide being encoded by the nucleic acid molecule of the invention and which is obtainable by the process described above.

The invention further relates to a process for obtaining an enzyme preparation comprising a polypeptide, which has serine protease activity, said process comprising the steps of culturing a host cell carrying the expression vector of the invention and either recovering the polypeptide from the cells or separating the cells from the culture medium and obtaining the supernatant having serine protease activity.

The present invention relates also to an enzyme preparation, which comprises the serine protease enzyme variant or variants as described above. The enzyme preparation or composition has serine protease activity and is obtainable by the process according to the invention.

Within the invention is an enzyme preparation as well as composition comprising the serine protease variant or variants of the invention.

The enzyme preparation or composition (e.g. detergent formulation) containing the protease enzyme variant or variants of the invention may further comprise other enzymes selected from the group consisting of proteases (other protease than that of the invention), amylases, lipases, cellulases, cutinases, pectinases, polygalacturonases, pectate lyases, pectinolytic enzymes, esterases, phytases, arabinases, galactanases, xanthanases, xyloglucanases, DNAses, mannanases, xylanases and oxidases, such as a laccase or peroxidase with or without a mediator. These enzymes are expected to enhance the performance of the serine proteases of the invention e.g. by removing the carbohydrates and oils or fats present in the material to be handled. Said enzymes may be natural or recombinant enzymes produced by the host strain or may be added to the culture supernatant or preparation or composition after the production process.

Said enzyme preparation or composition may further comprise one or more suitable additives selected from the group consisting of surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anticorrosion agents, hydrotropes, fabric hueing agents, dispersants, dye transfer inhibiting agents, fluorescent whitening agents, soil release polymers, anti-redepositions agents, anti-shrink agents, anti-wrinkling agents, bactericides, binders, carriers, dyes, enzyme stabilizers, fabric softeners, fillers, foam regulators, perfumes, pigments, buffers, preservatives, sod suppressors, solvents, and structurants for liquid detergents, structure elasticizing agents, enzyme inhibitors or stabilizers, enzyme activators, transferase(s), hydrolytic enzymes, oxido reductases, bluing agents and fluorescent dyes, antioxidants, and solubilizers.

Surfactants are useful in emulsifying grease and wetting surfaces. The surfactant may be a non-ionic including semipolar and/or anionic and/or cationic and/or zwitterionic. Buffers may be added to the enzyme preparation or composition to modify pH or affect performance or stability of other ingredients. Suitable stabilizers include polyols such as propylene glycol, or glycerol, a sugar or sugar alcohol, sorbitol, or hexylene glycol, lactic acid, boric acid, or boric acid derivatives, formic acid, aromatic borate ester, phenyl boronic acid derivative, peptide, other reversible subtilisin inhibitors or a combination thereof.

Bleaching agent is used to oxidize and degrade organic compounds. Examples of suitable chemical bleaching systems are $H_2O_2$ sources, such as perborate or percarbonate with or without peracid-forming bleach activators such as tetraacetylethylenediamine, or alternatively peroxyacids, e.g. amide, imide or sulfone type. Chemical oxidizers may be replaced partially or completely by using oxidizing enzymes, such as laccases or peroxidases. Many laccases do not function effectively in the absence of mediators.

Builders or complexing agents include substances, such as zeolite, diphosphate, triphosphate, carbonate, citrate, etc. The enzyme preparation may further comprise one or more polymers, such as carboxymethylcellulose, poly(ethylene glycol), poly(vinyl alcohol), poly(vinylpyrrolidone), etc. Also, softeners, caustics, preservatives for preventing spoilage of other ingredients, abrasives and substances modifying the foaming and viscosity properties can be added.

According to one preferred embodiment of the invention said enzyme preparation or composition comprising said enzyme variant is in the form of liquid composition or a solid composition such as solution, dispersion, paste, powder, granule, granulate, coated granulate, tablet, cake, crystal, crystal slurry, gel or pellet. According to a preferred embodiment of the invention said composition is a in liquid detergent or a solid detergent preferably in a form of a bar, a homogenous tablet, a tablet having two or more layers, a pouch having one or more compartments, a regular or compact powder, a granule, a granulate, a paste, a gel, or a regular, compact or concentrated liquid. Further, the enzyme variant in the preparation or composition may be in the form of immobilized enzyme.

The serine protease of the present invention may like other proteases, particularly alkaline proteases be used in the detergent, protein, brewing, meat, photographic, leather, dairy and pharmaceutical industries (Kalisz, 1988; Rao et al., 1998). For example, it may be used as an alternative to chemicals to convert fibrous protein waste (e.g. horn, feather, nails and hair) to useful biomass, protein concentrate or amino acids (Anwar and Saleemuddin, 1998). The use of the serine protease of the present invention may like other proteases prove successful in improving leather quality and in reducing environmental pollution and saving energy and it may be useful in synthesis of peptides and resolution of the mixture of D,L-amino acids. Subtilisin in combination with broad-spectrum antibiotics in the treatment of burns and wounds is an example of the use of serine proteases in pharmaceutical industry, therefore the fungal serine protease of the present invention may also find such use and may also be applicable in removal of blood on surgical equipments and cleaning contact lenses or dentures. Like alkaline protease from *Conidiobolus coronatus*, the fungal serine protease variant of the present invention may be used for replacing trypsin in animal cell cultures. The proteases of the invention can also be used in cleaning of membranes and destruction of biofilms. In baking the proteases can be used e.g. in destruction of the gluten network and in other food applications in hydrolysis of food proteins, e.g. proteins in milk. They can also be used e.g. in treating yeast, rendering (extracting more protein from animal bones), creating new flavours, reducing bitterness, changing emulsifying properties, generating bioactive peptides and reducing allergenicity of proteins. The substrates include animal, plant and microbial proteins.

Detergent industry, particularly the laundry detergent industry, has emerged as the single major consumer of proteases active at high pH range (Anwar and Saleemuddin, 1998). The ideal detergent protease should possess broad substrate specificity to facilitate the removal of large variety of stains due to food, grass, blood and other body secretions. It has to be active in the pH and ionic strength of the detergent solution, the washing temperature and pH, and tolerate mechanical handling as well as the chelating and oxidizing agents added to detergents. Due to awareness for energy conservation, it is currently desirable to use the protease at lower temperatures.

The present invention relates also to the use of the serine protease enzyme variant or the enzyme variant preparation for detergents, treating textile fibers, for treating proteinaceous materials, such as wool, hair, silk, leather, for treating feed or food, or for any application involving modification, degradation or removal of proteinaceous material.

One preferred embodiment of the invention is therefore the use of the serine protease enzyme variant as characterized above as a detergent additive useful for laundry detergent and dish wash compositions, including automatic dish washing compositions.

The expression "detergent" is used to mean substance or material intended to assist cleaning or having cleaning properties. The term "detergency" indicates presence or degree of cleaning property. The degree of cleaning property can be tested on different proteinaceous or protein containing substrate materials or stains or stain mixtures bound to solid, water-insoluble carrier, such as textile fibers or glass. Typical proteinaceous material includes blood, milk, ink, egg, grass and sauces. For testing purposes variety of proteinaceous stains are commercially available. The function of the detergent enzyme is to degrade and remove the protein-containing stains. Test results depend on the type of stain, the composition of the detergent and the nature and status of textiles used in the washing test (Maurer, 2004).

In the present invention the term "detergent stability" means that the enzyme or enzyme variant sufficiently retains its activity in detergent solution, during storage and/or washing. Therefore, it is efficient in degrading or removing stains or material in the presence of a detergent). The stability may be assayed by determining the residual activity e.g. after several days' incubation (at 37° C.) in detergent. The stability could be measured by various, enzyme specific activity measurements or as wash performance by application tests.

The term "effective amount" of a serine protease refers to the quantity of the protease enzyme necessary to achieve the enzymatic activity in the specific detergent composition. Preferably the detergent composition of the invention comprises from about 0.0001% to about 10% by weight of the detergent composition of a protease variant of the invention (as enzyme protein), more preferably from 0.001% to about 1%, still more preferably from 0.001% to about 0.5%.

Typically, the wash performance of protease is measured as "stain removal efficiency" or "stain removal effect" or "degree of cleaning property" meaning a visible and measurable increase of lightness or change in colour of the stained material, e.g. in artificially soiled swatches or test cloths. Lightness or change in colour values can be measured, for example by measuring the colour as reflectance values with a spectrophotometer using L*a*b* colour space coordinates. Fading or removal of proteinaceous stain indicating of the protease performance (stain removal effect or efficiency) is calculated for example as ΔL*, which means lightness value L* of enzyme treated fabric minus lightness value L* of fabric treated with washing liquor without enzyme (enzyme blank or control). The presence of detergent may improve the performance of the enzyme in removing the stains. The serine protease of the present invention degrades various kinds of proteinaceous stains (Cocoa (E-112), blood/milk/ink, Co+PES (E-117), blood/milk/ink, Co (E-116), grass (E-164, full egg with pigment (C-S-37), egg yolk with pigment (C-S-38), chocolate milk soot (C-03) and groundnut oil, milk (C-10)) under alkaline conditions in the presence of detergent (Example 2).

The object of the present invention is to provide novel *Malbranchea* protease variants that have better performance for stain removal (such as blood-milk-ink, full egg with pigment and egg yolk with pigment) as compared to the commercial enzymes and wild type *Malbranchea* protease, while the stability of the enzyme variants is as good or better as that of wild type *Malbranchea* protease. In addition, these variants of present invention are gentler to or less aggressive towards other enzymes like cellulases as shown in Example 3, FIG. 8 and FIG. 9.

In addition to washing, the enzyme variants of the present invention sufficiently retain their activity also during storage, even when stored in liquid detergents, as *Malbranchea* ALKO4122 protease (data not shown).

According to a preferred embodiment of the invention the fungal serine protease variants of the invention are useful in detergent liquids and detergent powders. The enzyme variant of enzyme preparation of the invention may be formulated for use in a hand or machine laundry or may be formulated for use in hard surface cleaning or in hand or machine dishwashing operations.

An aspect of the present invention is a recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2. A preferred aspect of the present invention is the recombinant serine protease enzyme, wherein, in the numbering according to SEQ ID NO: 2, said polypeptide has at least one amino acid substitution selected from Q103D and S105E. According to a more preferred aspect of the invention the recombinant serine protease enzyme's amino acid sequence corresponds to one of the amino acid sequences specified in SEQ ID NO: 4, SEQ ID NO: 6 or SEQ ID NO: 8.

An isolated nucleic acid molecule comprising a polynucleotide sequence which encodes a serine protease enzyme selected from the group consisting of: (a) a nucleic acid molecule encoding a polypeptide having serine protease activity and comprising the amino acid sequence as depicted in SEQ ID NO: 4 or SEQ ID NO: 6 or SEQ ID NO: 8; and (b) a nucleic acid molecule comprising the coding sequence of the nucleotide sequence as depicted in SEQ ID NO: 3 or SEQ ID NO: 5 or SEQ ID NO: 7 is also an aspect of this invention.

Another aspect of the invention is a recombinant expression vector comprising the isolated nucleic acid which encodes a serine protease enzyme selected from the group consisting of: (a) a nucleic acid molecule encoding a polypeptide having serine protease activity and comprising the amino acid sequence as depicted in SEQ ID NO: 4 or SEQ ID NO: 6 or SEQ ID NO: 8; and (b) a nucleic acid molecule comprising the coding sequence of the nucleotide sequence as depicted in SEQ ID NO: 3 or SEQ ID NO: 5 or SEQ ID NO: 7 operably linked to sequences capable of directing expression and secretion of said serine protease enzyme in a suitable host. Also, an aspect of the invention is an enzyme preparation, which comprises the recombinant serine protease enzyme. A preferred aspect of the invention is the enzyme preparation comprising other enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

Another preferred aspect of the invention is the enzyme preparation comprising one or more additives selected from the group consisting of stabilizers, buffers, surfactants, builders, bleaching agents, mediators, anti-corrosion agents, antiredeposition agents, caustics, abrasives, optical brighteners, dyes, perfumes, pigments, and preservatives, according to one preferred embodiment, the enzyme preparation is in the form of liquid composition or a solid composition such as solution, dispersion, paste, powder, granule, granulate, coated granulate, tablet, cake, crystal, crystal slurry, gel or pellet.

A host cell comprising this recombinant expression vector according to the invention is one aspect of the invention. Preferably, the host is a microbial host. More preferably, said host is a filamentous fungus. Evan more preferably, said host is of a genus *Trichoderma, Aspergillus, Fusarium, Humicola, Chrysosporium, Neurospora, Rhizopus, Penicillium, Myceliophthora* and *Mortierella*. Most preferably, said host is *T. reesei*.

One aspect of the invention is a process for producing a protease enzyme, the method comprising the step of introducing an amino acid substitution Q103D and/or S105E into the sequence which comprises an amino acid sequence having at least 70% identity to the amino acid sequence as defined in SEQ ID NO: 2. One preferred aspect of the invention is this process of producing a protease enzyme, wherein said process further comprises the steps of culturing the host cell and recovering the enzyme.

According to a preferred embodiment, the recombinant serine protease enzyme or the enzyme preparation according to the present invention can be used for detergents, for treating fibers, for treating proteinaceous materials, for treating food or feed, or for applications involving modification, degradation or removal of proteinaceous material. Preferred embodiment is the use of the recombinant serine protease enzyme or the enzyme preparation according to the present invention as a detergent additive. Still another preferred embodiment is the use of the recombinant serine protease enzyme or the enzyme preparation in liquid detergent or a solid detergent preferably in a form of a bar, a homogenous tablet, a tablet having two or more layers, a pouch having one or more compartments, a regular or compact powder, a granule, a granulate, a paste, a gel, or a regular, compact or concentrated liquid.

A detergent composition, characterized in that said composition comprises surfactants, the recombinant serine protease enzyme or the enzyme preparation according to the present invention, and additives selected from the group consisting of stabilizers, buffers, builders, bleaching agents, mediators, anti-corrosion agents, antiredeposition agents, caustics, abrasives, optical brighteners, dyes, perfumes, pigments, and preservatives, is also a preferred aspect of the present invention. The detergent composition which comprises other enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator is still another preferred aspect of the invention.

An aspect of the invention is a recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2. A preferred aspect of the invention is a recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2, wherein, in the numbering according to SEQ ID NO: 2, said polypeptide has at least one amino acid substitution selected from Q103D and S105E. A still more preferred aspect of the present invention is a recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2, wherein its amino acid sequence corresponds to one of the amino acid sequences specified in SEQ ID NO: 4, SEQ ID NO: 6 or SEQ ID NO: 8.

An isolated nucleic acid molecule comprising a polynucleotide sequence which encodes a serine protease enzyme selected from the group consisting of: (a) a nucleic acid molecule encoding a polypeptide having serine protease activity and comprising the amino acid sequence as depicted in SEQ ID NO: 4 or SEQ ID NO: 6 or SEQ ID NO: 8; and (b) a nucleic acid molecule comprising the coding sequence of the nucleotide sequence as depicted in SEQ ID NO: 3 or SEQ ID NO: 5 or SEQ ID NO: 7 is also an aspect of the present invention.

Further, a recombinant expression vector comprising the isolated nucleic acid comprising a polynucleotide sequence which encodes a serine protease enzyme selected from the group consisting of: (a) a nucleic acid molecule encoding a polypeptide having serine protease activity and comprising the amino acid sequence as depicted in SEQ ID NO: 4 or SEQ ID NO: 6 or SEQ ID NO: 8; and (b) a nucleic acid molecule comprising the coding sequence of the nucleotide sequence as depicted in SEQ ID NO: 3 or SEQ ID NO: 5 or SEQ ID NO: 7 operably linked to regulatory sequences capable of directing expression of said serine protease enzyme in a suitable host is an aspect of the present invention.

A host cell comprising the recombinant expression vector comprising the isolated nucleic acid comprising a polynucleotide sequence which encodes a serine protease enzyme selected from the group consisting of: (a) a nucleic acid molecule encoding a polypeptide having serine protease activity and comprising the amino acid sequence as depicted in SEQ ID NO: 4 or SEQ ID NO: 6 or SEQ ID NO: 8; and (b) a nucleic acid molecule comprising the coding sequence of the nucleotide sequence as depicted in SEQ ID NO: 3 or SEQ ID NO: 5 or SEQ ID NO: 7 operably linked to regulatory sequences capable of directing expression of said serine protease enzyme in a suitable host is an aspect of the present invention. According to a more preferred aspect of the invention the host cell is a microbial host cell. According to an even more preferred aspect of the invention the host cell is a filamentous fungus. The host cell being of a genus *Trichoderma, Aspergillus, Fusarium, Humicola, Chrysosporium, Neurospora, Rhizopus, Penicillium, Myceliophthora* and *Mortierella* is a still more preferred aspect of the invention. According to the most preferred aspect of the invention, the host cell is *T. reesei*.

An aspect of the present invention is a process for producing a protease enzyme, the method comprising the step of introducing an amino acid substitution Q103D and/or S105E into the sequence which comprises an amino acid sequence having at least 70% identity to the amino acid sequence as defined in SEQ ID NO: 2.

According to a more preferred aspect the process of producing a protease enzyme further comprises the steps of culturing the host cell comprising the recombinant expression vector comprising the isolated nucleic acid comprising a polynucleotide sequence which encodes a serine protease enzyme selected from the group consisting of: (a) a nucleic acid molecule encoding a polypeptide having serine protease activity and comprising the amino acid sequence as depicted in SEQ ID NO: 4 or SEQ ID NO: 6 or SEQ ID NO: 8; and (b) a nucleic acid molecule comprising the coding sequence of the nucleotide sequence as depicted in SEQ ID NO: 3 or SEQ ID NO: 5 or SEQ ID NO: 7 operably linked to regulatory sequences capable of directing expression of said serine protease enzyme in a suitable host and recovering the enzyme.

An enzyme preparation, which comprises the recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2. According to a more preferred aspect of the invention, the enzyme preparation comprises other enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

According to an even more preferred aspect, the enzyme preparation comprises one or more additives selected from the group consisting of stabilizers, buffers, surfactants, builders, bleaching agents, mediators, anti-corrosion agents, antiredeposition agents, caustics, abrasives, optical brighteners, dyes, perfumes, pigments, and preservatives. According to the most preferred aspect the enzyme preparation is in the form of liquid composition or a solid composition such as solution, dispersion, paste, powder, granule, granulate, coated granulate, tablet, cake, crystal, crystal slurry, gel or pellet.

An aspect of the invention is a use of the recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2 or the enzyme preparation, which comprises the recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2 for detergents, for treating fibers, for treating proteinaceous materials, for treating food or feed, or for applications involving modification, degradation or removal of proteinaceous material.

According to a preferred aspect of the invention, the proteinaceous materials is selected from wool, hair, leather and silk. According to an even more preferred aspect of the invention the enzyme preparation is used as a detergent additive. According to the most preferred aspect of the invention is the use of the recombinant serine protease enzyme or the enzyme preparation in liquid detergent or a solid detergent preferably in a form of a bar, a homogenous tablet, a tablet having two or more layers, a pouch having one or more compartments, a regular or compact powder, a granule, a granulate, a paste, a gel, or a regular, compact or concentrated liquid.

Also a detergent composition that comprises surfactants, the recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2 or the enzyme preparation, which comprises the recombinant serine protease enzyme comprising an amino acid sequence having at least 70% identity to an amino acid sequence as defined in SEQ ID NO: 2 and which comprises amino acid D at position 103 and/or amino acid E at position 105 in the numbering according to SEQ ID NO: 2, and additives selected from the group consisting of stabilizers, buffers, builders, bleaching agents, mediators, anti-corrosion agents, antiredeposition agents, caustics, abrasives, optical brighteners, dyes, perfumes, pigments, and preservatives, is an aspect of the invention.

A further aspect of the invention is the detergent composition comprising other enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses and oxidases, with or without a mediator.

As a conclusion, novel fungal serine protease enzyme variants are provided, originating from a thermophilic micro-organism, and which are compatible and stable in liquid detergent compositions and less aggressive for other enzymes, whereby less stabilizing and other additives are needed.

The invention is illustrated with the following examples relating to some embodiments of the invention; however, the invention is not meant to be limited to these examples only.

EXAMPLES

Example 1. Design and Production of *Malbranchea* Protease Variants in *Trichoderma reesei*

Three *Malbranchea* protease variants, named as M59 (Q103D), M60 (S105E) and M61 (Q103D; S105E) (Table 1) were designed basing on the amino acid sequence of the mature wild-type *Malbranchea* ALKO4122 protease, designated here as M0 (nucleic acid sequence encoding the amino acid sequence of mature *Malbranchea* ALKO4122 protease SEQ ID NO: 1, deduced amino acid sequence SEQ ID NO: 2). Synthetic variant genes, each including the native signal and pro-sequence encoding nucleotide sequences of the *Malbranchea* ALKO4122 protease (SEQ ID NO: 9; FIGS. 1A and B) and variant mature encoding sequence (see Table 1 for the SEQ ID numbers) were ordered from GenScript. The synthetic genes also included, in their 5'- and 3'-ends, *T. reesei* sequences enabling correct fusion to the cbh1 promoter (SacII site included in the chh1 promoter and chh1 promoter sequence from SacII to end of promoter) and chh1 terminator (sequence following the chh1 STOP codon to AgeI site in the terminator and AgeI site). For the *T. reesei* genome sequence and gene organization see genome.jgi.doe.gov/Trire2/Trire2.home.html. The synthetic genes were cleaved from the commercial GenScript vector and expression cassettes were constructed for production of the recombinant protease variants (FIG. 2, Table 1) by ligating the synthetic genes to SacII-AgeI digested expression vector using standard molecular biology methods. In the final expression cassettes, the synthetic genes encoding the full-length protease variants were fused to *T. reesei* chh1 (cel7A) promoter and terminator (exact fusions) similarly to the constructions described in Paloheimo et al. (2003). Synthetic amdS gene encoding the *Aspergillus nidulans* acetamidase (AmdS) was used as a transformation marker in the expression cassettes (FIG. 2).

TABLE 1

Information on the synthetic genes designed and used in construction of the expression cassettes for production of the *Malbranchea* protease variants in *T. reesei*. The SEQ ID numbers for the mature protease encoding nucleotide sequences, the mature amino acid sequences and mutated amino acid positions are numbered by correspondence with the mature *Malbranchea* protease amino acid sequence without signal and pro-sequences (SEQ ID NO: 2). The triplet codons for D and E were chosen which are more frequently used by *T. reesei* of the two possible options (GAC and GAT for D, GAA and GAG for E).

| Variant designation | Mutation (codon change) | Deduced amino acid sequence SEQ ID NO: | Gene SEQ ID NO: | Expression plasmid |
|---|---|---|---|---|
| M59 | Q103D (CAG → GAC/GAT) | 4 | 3 | pALK4521 |
| M60 | S105E (TCA → GAG/GAA) | 6 | 5 | pALK4522 |
| M61 | Q103D, S105E (CAG → GAC/GAT, TCA → GAG/GAA) | 8 | 7 | pALK4523 |

The expression cassettes pALK4521, pALK4522 and pALK4523 (FIG. 2) were isolated from the vector backbones of the expression plasmids by NotI digestion and were used for transforming the *T. reesei* host strain. The transformations were performed to *T. reesei* protoplasts according to Penttilä et al. (1987) with the modifications described in Karhunen et al. (1993). The transformants were selected on plates containing acetamide as the sole nitrogen source. A set of transformants from each transformation was purified on selection plates through single conidia prior to sporulating them on potato dextrose (PD) agar.

For protease production the transformants were inoculated from the PD slants to 50 ml of complex lactose-based cellulase inducing medium (Joutsjoki et al., 1993) buffered with 5% $KH_2PO_4$ at pH 6.0, in 250 ml Erlenmeyer flasks. The untransformed host strain and a previously constructed transformant strain producing the recombinant wild-type *Malbranchea* protease (M0) were used as references in the cultivations. The protease production from the transformants was analyzed from the culture supernatants after growing them for 5 days at 30° C., 250 rpm.

All the three mutant proteases were well produced by *T. reesei*. In SDS-PAGE gels, a major protein band of approximately 30 kDa, corresponding to the expected molecular mass of the recombinant protease was detected from the spent culture supernatants. The protease activity was assayed using casein as a substrate as described in patent EP2691520B1, using optimized absorbance range of 0.1-0.5 (target 0.3-0.35) for this molecule. One protease unit (BPU) is comparable to an amount of enzyme activity, which under standard conditions in 1 minute releases from casein an amount of peptide fragments equal to 1 μg of tyrosine. Corresponding protease activities were obtained from the pALK4521, pALK4522 and pALK4523 transformants as from the reference transformant producing the recombinant wild-type *Malbranchea* protease.

The *T. reesei* transformants producing the best protease activities in the shake flask cultivations were cultivated in laboratory scale bioreactors. Cellulase inducing complex medium was used in the cultivations. The spent culture media obtained from the shake flask or bioreactor cultivations was used in the application tests (Examples 2-3).

Example 2. Stain Removal Performance of *Malbranchea* ALKO 4122 Protease Variants in Liquid Detergent Shake flask cultivation samples of *Malbranchea* protease variants produced in *Trichoderma* (as described in Example 1), were tested for their ability to remove protease sensitive standard stains at 40° C. and water hardness of 16° dH with a commercial liquid detergent and compared to parental molecule M0. The following artificially soiled test cloths from Center for test material B.V. (the Netherlands), were used: Cocoa (E-112), blood/milk/ink, Co+PES (E-117), blood/milk/ink, Co (E-116), grass (E-164, full egg with pigment (C-S-37), egg yolk with pigment (C-S-38), chocolate milk soot (C-03) and groundnut oil, milk (C-10). The fabric was cut in 6 cm×6 cm swatches. Commercial Liquid detergent base without enzymes was used at concentration of 5 g per liter of wash liquor pH of the wash liquor was approximately 8.2. Proteases were dosed as enzyme activity units (BPU) correlating to μg tyrosine/min per ml wash liquor as described in Example 1. Control sample contained the detergent solution but no protease.

For synthetic tap water with hardness of 16° dH the following stock solutions were prepared in deionized water (Milli-Q or equivalent):

Stock solution with 1000° d Calcium-hardness: $CaCl_2 \times 2 H_2O$ (1.02382.1000, Merck KGaA, Germany) 26.22 g/l Stock solution with 200° d Magnesium-hardness: $MgSO_4 \times 7 H_2O$ (1.05886.1000, Merck KGaA, Germany) 8.79 g/l $H_2O$ $NaHCO_3$ stock solution: $NaHCO_3$ (1.06329.1000 Merck KGaA, Germany) 29.6 g/l 13.3 ml $CaCl_2$ solution, 13.3 ml $MgSO_4$ solution and 10.0 ml of freshly made $NaHCO_3$ solution were added in volumetric flask in the given order, made up to 1 liter with deionized water and mixed. The hardness of water was determined by complexometric titration and found correct.

Stain removal treatments were performed in Atlas LP-2 Launder-Ometer as follows. Launder-Ometer was first preheated to 40° C. Then detergent, 250 ml synthetic tap water with hardness of 16° dH and diluted enzyme (<1.0 ml) were added into 1.2-liter containers. Stains were added and the Launder-Ometer was run at 40° C. for 60 min with a rotation speed of 42 rpm. Stains E-112, E-116, E-117 and E-164 were together in a same container and the rest of the stains in another. After that the swatches were carefully rinsed under running water and dried overnight at indoor air, on a grid protected against daylight.

The stain removal effect was evaluated by measuring the colour as reflectance values with Konica Minolta CM-3610A spectrophotometer using L*a*b* color space coordinates (illuminant D65/10°, 420 nm cut). Fading of the stains, indicating protease performance (stain removal efficiency) was calculated as ΔL* (delta L*), which means lightness value L* of enzyme treated fabric minus lightness value L* of fabric treated with washing liquor without protease (control). Final results (total stain removal effect) were shown as sum of ΔL* of each stain.

Figure 3:
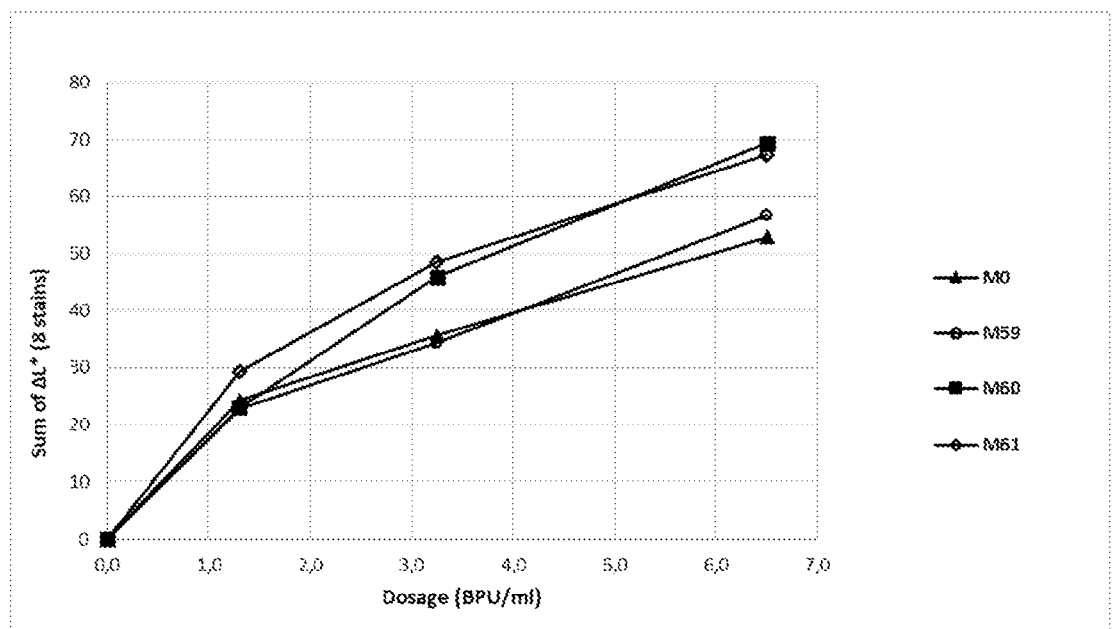
FIG. 3 schematically shows the stain removal performance of M0 variants compared to parental molecule M0 as sum of ΔL* of 8 stains. Washing conditions in Launder-Ometer: 40° C., 16° dh, 60 min, commercial liquid detergent 5 g/l, pH approx. 8.2.
Figure 4:
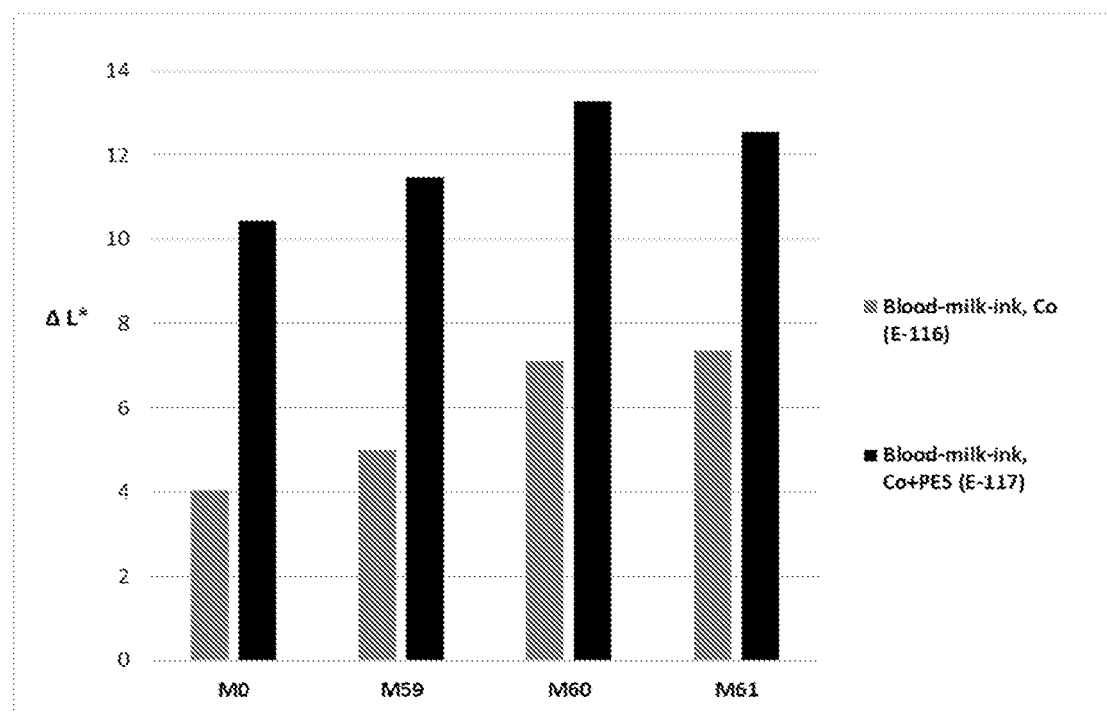
FIG. 4 shows the stain removal effect of M0 variants and parental molecule M0 as ΔL* on blood-milk-ink stains with dosage of 6.5 BPU per ml of wash liquor. Washing conditions in Launder-Ometer: 40° C., 16° dh, 60 min, commercial liquid detergent 5 g/l, pH approx. 8.2.
Figure 5:
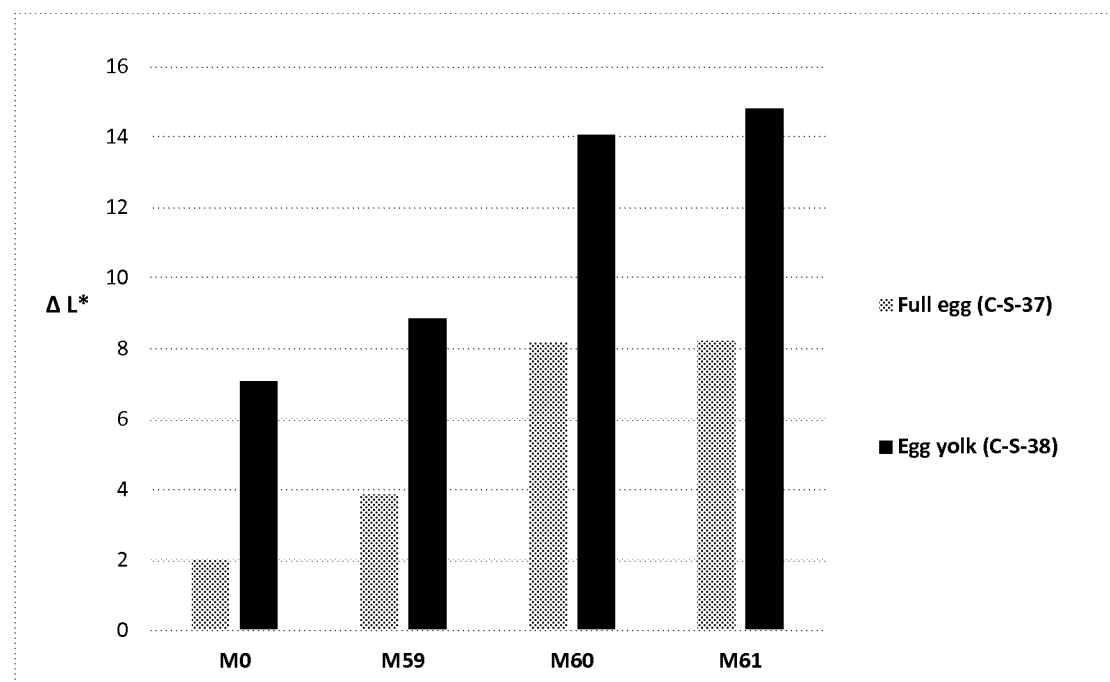
FIG. 5 shows the stain removal effect of M0 variants and parental molecule M0 as ΔL* on egg stains with dosage of 6.5 BPU per ml of wash liquor. Washing conditions in Launder-Ometer: 40° C., 16° dh, 60 min, commercial liquid detergent 5 g/l, pH approx. 8.2.

The best stain removal effect (as a sum of ΔL* of 8 stains) was obtained with the shake flask supernatants of variants M60 and M61, as shown in FIG. 3. The performance compared to parental molecule M0 was surprisingly improved especially on blood-milk-ink and egg stains (FIGS. 4 and 5).

Figure 6:
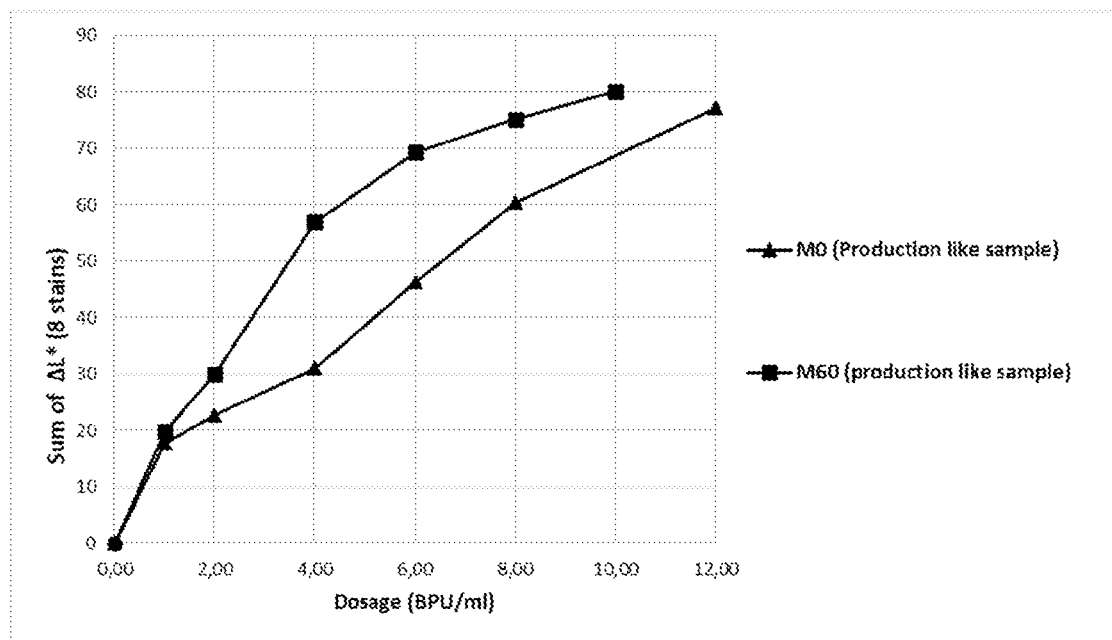
FIG. 6 shows the stain removal performance of production like samples of variant M60 compared to parental molecule M0 as sum of ΔL* of 8 stains. Washing conditions in Launder-Ometer: 40° C., 16° dh, 60 min, commercial liquid detergent 5 g/l, pH approx. 8.2.
Figure 7A:
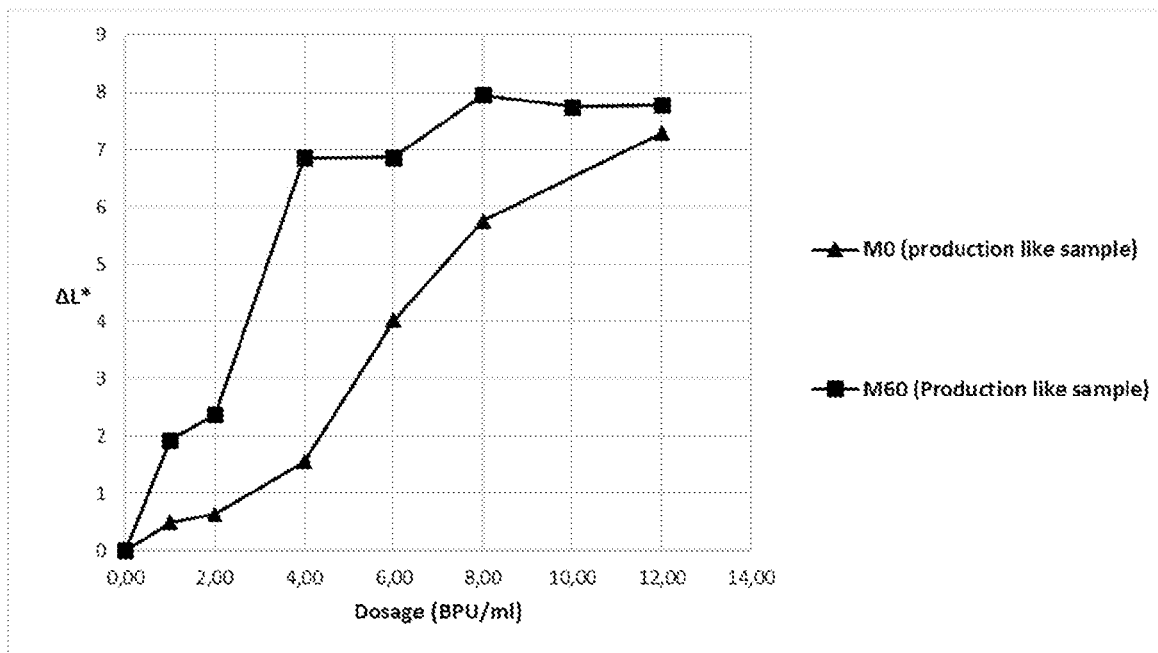
FIG. 7A shows the stain removal effect of production like samples of M0 variants and parental molecule M0 as ΔL* on blood-milk-ink, CO (E-116). Washing conditions in Launder-Ometer: 40° C., 16° dh, 60 min, commercial liquid detergent 5 g/l, pH approx. 8.2.
Figure 7B:
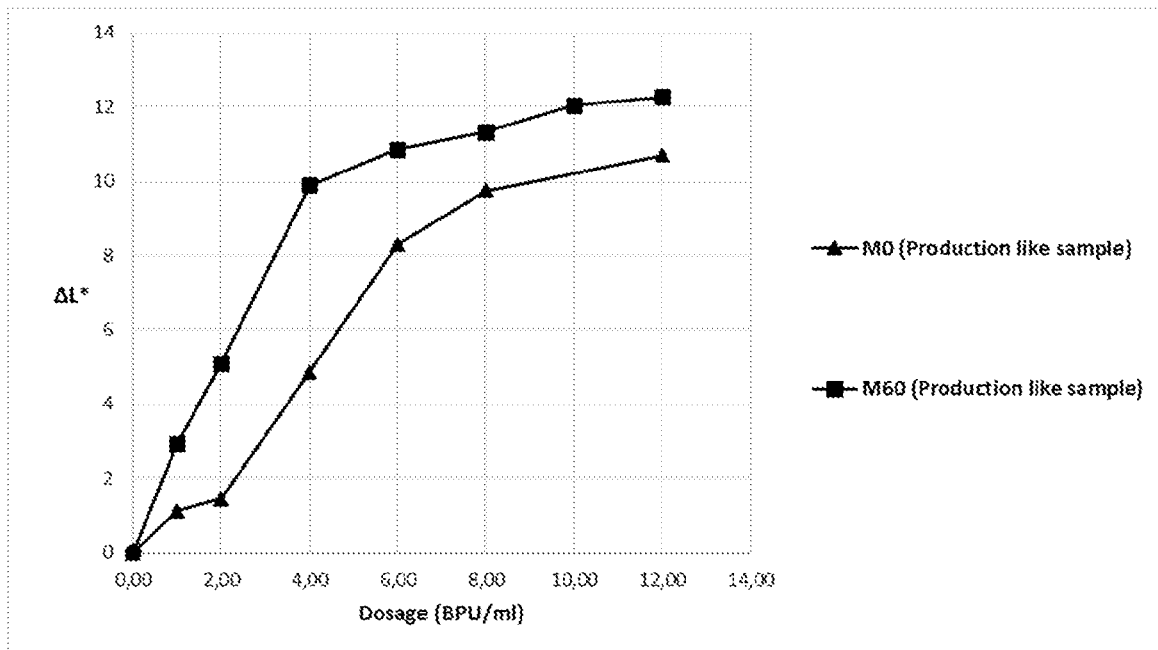
FIG. 7B shows the stain removal effect of production like samples of M0 variants and parental molecule M0 as ΔL* on blood-milk-ink, CO+PES (E-117). Washing conditions in Launder-Ometer: 40° C., 16° dh, 60 min, commercial liquid detergent 5 g/l, pH approx. 8.2.
Figure 7C:
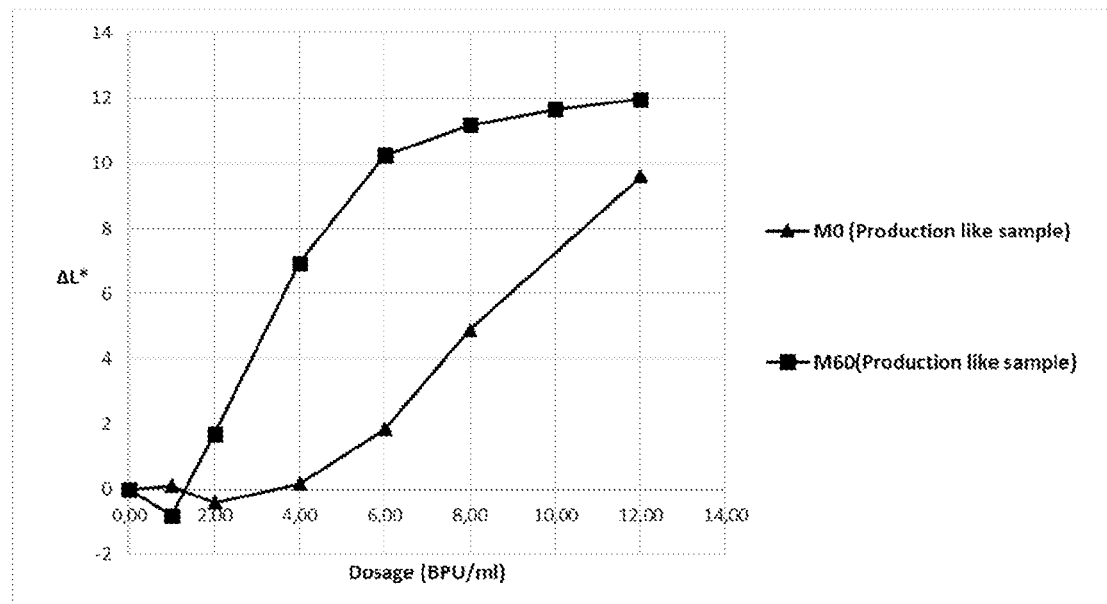
FIG. 7C shows the stain removal effect of production like samples of M0 variants and parental molecule M0 as ΔL* on full egg with pigment, CO (C-S-37). Washing conditions in Launder-Ometer: 40° C., 16° dh, 60 min, commercial liquid detergent 5 g/l, pH approx. 8.2.
Figure 7D:
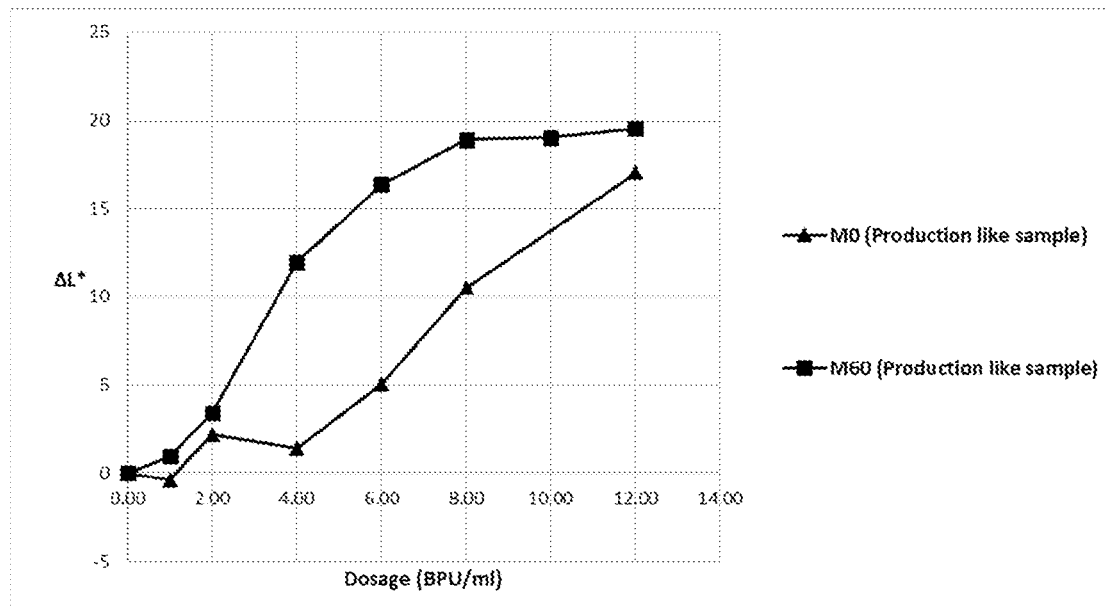
FIG. 7D shows the stain removal effect of production like samples of M0 variants and parental molecule M0 as ΔL* on egg yolk with pigment, CO (C-S-38). Washing conditions in Launder-Ometer: 40° C., 16° dh, 60 min, commercial liquid detergent 5 g/l, pH approx. 8.2.

Tests were carried out also with a production like sample of M60 from pilot cultivation using similar test system as described above but having broader dosing range (0-12 BPU/ml wash liquor), representing a typical dosing range of commercial proteases (0.1-1% enzyme product of detergent weight). Results obtained with the production like sample of M0 confirmed that the stain removal performance of M60 was considerably better compared to parental molecule M0 (FIG. 6), especially with blood-milk-ink (FIGS. 7A and 7B) and full egg (FIG. 7C) and egg yolk (FIG. 7D) stains.

Example 3. Degrading Effect of Protease Variants on Commercial Cellulase in a Liquid Detergent at 37° C.

Shakeflask cultivation supernatants of M0 variants, produced in *Trichoderma* as described in Example 1, were tested based on their degrading effect on a commercial cellulase at 37° C. in a liquid detergent. Parental molecule M0 was used as reference. An amount of protease, corresponding to activity of 520 BPU/g, was added to a liquid screening detergent containing 1% (w/w) of the commercially available cellulase BIOTOUCH® DCL (by AB Enzymes). Protease activity was measured as described in Example 1. The composition of the detergent is described in Table 2. Samples in plastic tubes with caps were incubated at 37° C. for 7 days. The cellulase activity was measured after incubation as the release of reducing sugars from carboxymethylcellulose (3% CMC) at 50° C. in 50 mM HEPES buffer pH 7.0 essentially as described by Bailey and Nevalainen, 1981; Haakana, et al, 2004 (NCU activity). Results were calculated as relative residual cellulase activity, which was obtained by dividing the residual activity of M61 containing sample after incubation at 37° C. by than that of parental molecule M0 containing sample. Residual activity (%) was calculated by dividing the activity of a sample after incubation at 37° C. by the initial activity of the sample. In addition to cellulase activity (NCU, the residual protease activity (BPU) of the samples was measured as well after 7 days, using the method described in Example 1.

TABLE 2

Composition of a liquid detergent formulation.

| Ingredient | % |
|---|---|
| Anionic surfactants | 10-20 |
| Nonionic surfactants, soap | 5-10 |
| Boric acid | ≤1 |
| Propylene glycol | 4-8% |
| Ethanol | 2-5% |
| pH 8.0-8.4 | |

Figure 8:
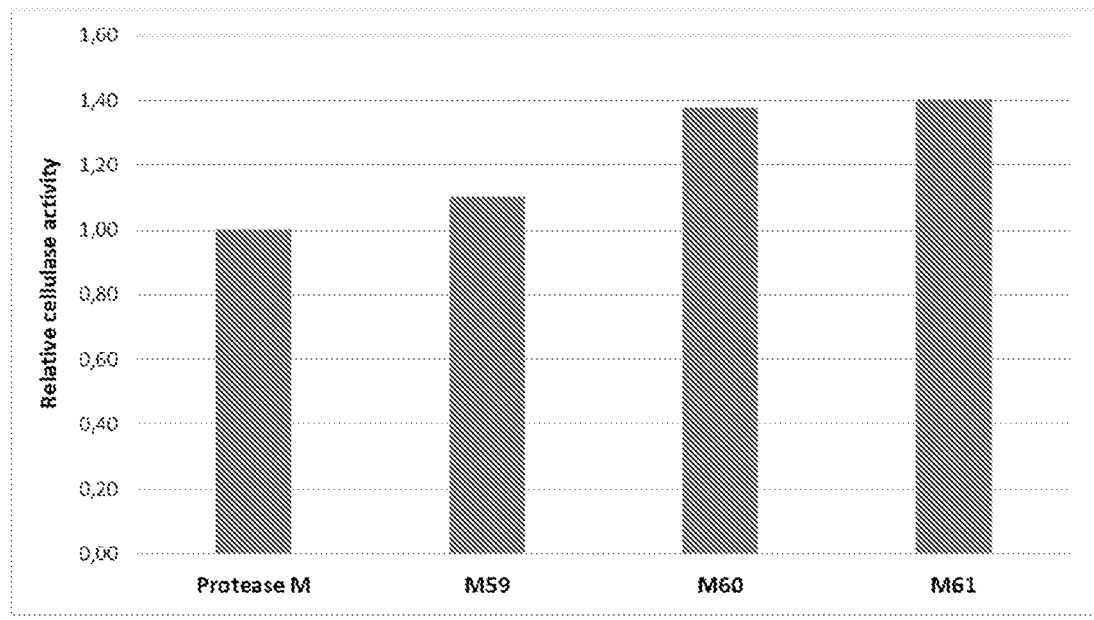
FIG. 8 describes the degrading effect of M0 variants (cultivation samples) to a commercial cellulase (1%) in a liquid detergent at 37° C. and 7 d, using an amount of protease corresponding to activity of 520 BPU/g. Stability of cellulase is shown as relative residual activity after storage compared to the solution containing parental molecule M0 as protease.
Figure 9:
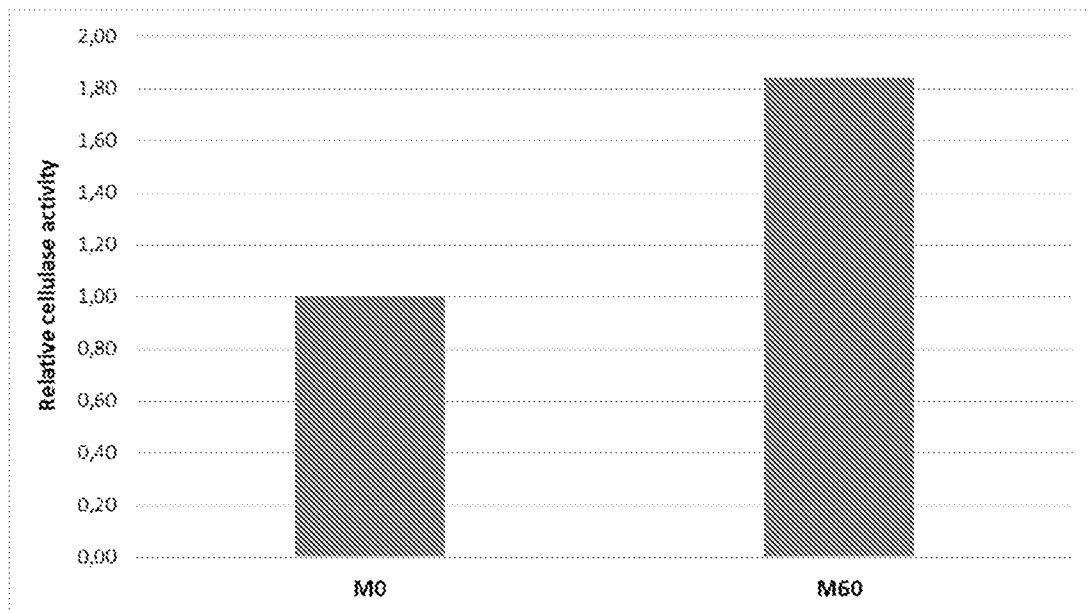
FIG. 9 describes the degrading effect of production like samples of variant M60 and M0 cellulase (1%) in a liquid detergent at 37° C. and 7 d), using a high amount of protease corresponding to activity of 2080 BPU/g. Stability of cellulase is shown as relative residual activity after storage compared to the solution containing parental molecule M0 as protease.

Based on results shown in FIG. 8, the stability of cellulase was improved in the presence of variant proteases in liquid detergent at 37° C. without significant changes in the protease activity compared to parental molecule M0 (data was not shown). Best cellulase stability was obtained using shake flask cultivation samples of protease variants M60 and M61, with them the stability of cellulase activity was improved approx. 1.4 times, when protease was added 520 BPU/g in detergent.

Stability tests were carried out also with a production like sample of M60 from pilot cultivation using similar test system as described above but having high amount of protease corresponding to 2080 BPU per g of detergent. Parental molecule M0 was used as reference.

Results obtained with the production like sample of M60 confirmed that also with high protease amount there was considerably more cellulase activity left (about 1.8×) compared to parental molecule M0 (FIG. 9), without significant changes in the residual protease activity (data not shown) during 7 or 14 days. Results of these tests indicate that variants of this invention with improved wash performance (stain removal effect) are also less aggressive to cellulase than parental molecule M0.

REFERENCES

Anwar, A and M Saleemuddin. 1998. Alkaline proteases: A review. Bioresource Technology 64:175-183.

Bailey M and Nevalainen H. 1981. Induction, isolation and testing of stable *Trichoderma reesei* mutants with improved production of solubilizing cellulase. Enzyme Microb. Technol. 3:153-157.

Chen, Y-J, and M Inouye, 2008. The intramolecular chaperone-mediated protein folding. Curr. Opin. Struct. Biol. 18: 765-770.

Cherry, J. R., and Fidantsef, A. L. 2003. Directed evolution of industrial enzymes: an update. Curr. Opin. Biotechnol. 14: 438-443.

Gaucher G M, Stevenson K J 2004. Thermomycolin. Handbook of Proteolytic Enzymes 2$^{nd}$ Ed.:

Gupta, R, Q K Beg, S Khan and B Chauhan. 2002. An overview on fermentation, downstream processing and properties of microbial alkaline protease. Appl. Microbiol. Biotechnol. 60: 381-395.

Haakana H, Miettinen-Oinonen A, Joutsjoki V, Mäntylä A, Suominen P and Vehmaanperä J. 2004. Cloning of cellulase genes from *Melanocarpus albomyces* and their efficient expression in *Trichoderma reesei*. Enzyme Microb. Technol. 34:159-167.

Joutsjoki, V. V., T. K. Torkkeli, and K. M. H. Nevalainen. 1993. Transformation of *Trichoderma reesei* with the *Hormoconis resinae* glucoamylase P (gamP) gene: production of a heterologous glucoamylase by *Trichoderma reesei*. Curr. Genet. 24:223-228.

Karhunen, T., A. Mäntylä, K. M. H. Nevalainen, and P. L. Suominen. 1993. High frequency one-step gene replacement in *Trichoderma reesei*. I. Endoglucanase I overproduction. Mol. Gen. Genet. 241:515-522.

Kalisz, H M. 1988. Microbial proteinases. Adv. Biochem. Eng. Biotechnol. 36:1-65.

Malardier L, M J Daboussi, J Julien, F Roussel, C Scazzocchio and Y Brygoo. 1989. Cloning of the nitrate reductase gene (niaD) of *Aspergillus nidulans* and its use for transformation of *Fusarium oxysporum*. Gene 78:147-156.

Maurer, K-H. 2004. Detergent proteases. Curr. Opin. Biotechnol. 15: 330-334.

Maurer, K-H, 2010. Enzymes, Detergent. pp. 1-17. In (M C Flickinger ed.) Encyclopedia of Industrial Biotechnology: Bioprocess, Bioseparation, and Cell Technology, John Wiley & Sons, Inc.

Ong P H and Gaucher G M, 1975. Production, purification and characterization of thermomycolase, the extracellular serine protease of the thermophilic fungus *Malbranchea pulchella* var. *sulfurea*. Can. J. Microbiol. 22: 165-175.

Paloheimo, M., A. Mäntylä, J. Kallio, and P. Suominen. 2003. High-yield production of a bacterial xylanase in the filamentous fungus *Trichoderma reesei* requires a carrier polypeptide with an intact domain structure. Appl. Env. Microbiol. 69:7073-7082.

Penttilä M, H Nevalainen, M Rättö, E Salminen, and J Knowles. 1987. A versatile transformation system for the cellulolytic filamentous fungus *Trichoderma reesei*. Gene 61:155-164.

Rao, M B, A M Tanksale, M S Ghatge and V V Deshpande. 1998. Molecular and biotechnological aspects of microbial proteases. Microbiol. Mol. Biol. Rev. 62:597-635.

The invention claimed is:

1. A polypeptide comprising an amino acid sequence having at least 82% identity to the sequence set forth in SEQ ID NO: 2, wherein the polypeptide has serine protease activity, and wherein the polypeptide comprises amino acid D at position 103, amino acid E at position 105, or amino acid D at position 103 and amino acid E at position 105 in the numbering according to SEQ ID NO: 2.

2. The polypeptide of claim 1, comprising an amino acid sequence having at least 95% identity to the sequence set forth in SEQ ID NO: 2, wherein the polypeptide comprises amino acid D at position 103, amino acid E at position 105, or amino acid D at position 103 and amino acid E at position 105 in the numbering according to SEQ ID NO: 2.

3. The polypeptide of claim 1, comprising an amino acid sequence having at least 96% identity to the sequence set forth in SEQ ID NO: 2, wherein the polypeptide comprises amino acid D at position 103, amino acid E at position 105, or amino acid D at position 103 and amino acid E at position 105 in the numbering according to SEQ ID NO: 2.

4. An isolated nucleic acid molecule comprising a polynucleotide sequence which encodes a serine protease enzyme selected from the group consisting of:
(a) a nucleic acid molecule encoding a polypeptide having serine protease activity and comprising the amino acid sequence set forth in SEQ ID NO: 4 or SEQ ID NO: 6 or SEQ ID NO: 8; and
(b) a nucleic acid molecule comprising the coding sequence of the nucleotide sequence set forth in SEQ ID NO: 3 or SEQ ID NO: 5 or SEQ ID NO: 7.

5. An expression vector comprising the isolated nucleic acid of claim 4 operably linked to regulatory sequences capable of directing expression of said serine protease enzyme in a host cell.

6. A host cell comprising the expression vector of claim 5.

7. The host cell of claim 6, wherein said host cell is a microbial host cell.

8. The host cell of claim 6, wherein said host cell is a filamentous fungus cell.

9. The host cell of claim 6, wherein said host cell is of a genus *Trichoderma, Aspergillus, Fusarium, Humicola, Chrysosporium, Neurospora, Rhizopus, Penicillium, Myceliophthora,* or *Mortierella*.

10. The host cell of claim 9, wherein said host is *T. reesei*.

11. A process for making a protease enzyme, the method comprising the step of introducing an amino acid substitution selected from the group consisting of Q103D, S105E, and Q103D and S105E, into the sequence which comprises an amino acid sequence having at least 82% identity to the sequence set forth in SEQ ID NO: 2.

12. A method of making a serine protease enzyme, said method comprising the steps of culturing the host cell of claim 6 and recovering the serine protease enzyme.

13. An enzyme preparation, which comprises the polypeptide of claim 1, and one or more additives selected from the group consisting of stabilizers, buffers, surfactants, builders, bleaching agents, mediators, anti-corrosion agents, antiredeposition agents, caustics, abrasives, optical brighteners, dyes, perfumes, pigments, and preservatives.

14. The enzyme preparation of claim 13, wherein said enzyme preparation comprises one or more other enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

15. The enzyme preparation of claim 13, wherein the one or more enzymes is a cellulase.

16. The enzyme preparation of claim 13, wherein said enzyme preparation is in the form of a liquid composition or a solid composition.

17. A method for (i) making a detergent, (ii) treating fibers; (iii) treating, modifying, degrading, and/or removing proteinaceous materials; or (iv) treating food or feed, the method comprising adding the polypeptide of claim 1 to the detergent, fibers, proteinaceous materials, or food or feed.

18. The method of claim 17, wherein the proteinaceous materials are selected from the group consisting of wool, hair, leather and silk.

19. A method of improving the stain removal ability of a liquid detergent or a solid detergent, the method comprising adding the polypeptide of claim 1 to the liquid detergent or the solid detergent.

20. A detergent composition, wherein said detergent composition comprises a detergent, one or more surfactants, the polypeptide of claim 1, and one or more additives selected from the group consisting of stabilizers, buffers, builders, bleaching agents, mediators, anti-corrosion agents, antiredeposition agents, caustics, abrasives, optical brighteners, dyes, perfumes, pigments, and preservatives.

21. The detergent composition according to claim 20, wherein said detergent composition comprises one or more enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses and oxidases, with or without a mediator.

22. A detergent composition, wherein said detergent composition comprises one or more surfactants, the enzyme preparation of claim 13, and one or more additives selected from the group consisting of stabilizers, buffers, builders, bleaching agents, mediators, anti-corrosion agents, antiredeposition agents, caustics, abrasives, optical brighteners, dyes, perfumes, pigments, and preservatives.

23. A method for (i) making a detergent; (ii) treating fibers; (iii) treating, modifying, degrading, and/or removing proteinaceous materials; or (iv) treating food or feed, the method comprising adding the enzyme preparation of claim 13 to the detergent, fibers, proteinaceous materials, or food or feed.

24. The enzyme preparation of claim 13, wherein said enzyme preparation is in the form of a solution, dispersion, paste, powder, granule, granulate, coated granulate, tablet, cake, crystal, crystal slurry, gel, or pellet.

25. The polypeptide of claim 1, comprising the amino acid sequence set forth in SEQ ID NO: 4.

26. The polypeptide of claim 1, comprising the amino acid sequence set forth in SEQ ID NO: 6.

27. The polypeptide of claim 1, comprising the amino acid sequence set forth in SEQ ID NO: 8.

28. An enzyme preparation, which comprises the polypeptide of claim 25, wherein said enzyme preparation comprises one or more additives selected from the group consisting of stabilizers, buffers, surfactants, builders, bleaching agents, mediators, anti-corrosion agents, antiredeposition agents, caustics, abrasives, optical brighteners, dyes, perfumes, pigments, and preservatives.

29. The enzyme preparation of claim 28, wherein said enzyme preparation comprises one or more other enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

30. An enzyme preparation, which comprises the polypeptide of claim 26, wherein said enzyme preparation comprises one or more additives selected from the group consisting of stabilizers, buffers, surfactants, builders, bleaching agents, mediators, anti-corrosion agents, antiredeposition agents, caustics, abrasives, optical brighteners, dyes, perfumes, pigments, and preservatives.

31. The enzyme preparation of claim 30, wherein said enzyme preparation comprises one or more other enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

32. An enzyme preparation, which comprises the polypeptide of claim 27, wherein said enzyme preparation comprises one or more additives selected from the group consisting of stabilizers, buffers, surfactants, builders, bleaching agents, mediators, anti-corrosion agents, antiredeposition agents, caustics, abrasives, optical brighteners, dyes, perfumes, pigments, and preservatives.

33. The enzyme preparation of claim 32, wherein said enzyme preparation comprises one or more other enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

34. A method of removing a stain from a fabric, the method comprising contacting the fabric with a detergent comprising the polypeptide of claim 1.

35. The method of claim 34, wherein the stain is a blood stain, a milk stain, an ink stain, and egg stain, a pigment stain, or an oil stain.

36. A method of removing a stain from a fabric, the method comprising contacting the fabric with a detergent comprising the polypeptide of claim 25.

37. The method of claim 36, wherein the stain is a blood stain, a milk stain, an ink stain, and egg stain, a pigment stain, or an oil stain.

38. A method of removing a stain from a fabric, the method comprising contacting the fabric with a detergent comprising the polypeptide of claim 26.

39. The method of claim 38, wherein the stain is a blood stain, a milk stain, an ink stain, and egg stain, a pigment stain, or an oil stain.

40. A method of removing a stain from a fabric, the method comprising contacting the fabric with a detergent comprising the polypeptide of claim 27.

41. The method of claim 40, wherein the stain is a blood stain, a milk stain, an ink stain, and egg stain, a pigment stain, or an oil stain.

42. A composition comprising (i) a detergent; and (ii) the polypeptide of claim 1.

43. The composition of claim 42, wherein the detergent is a liquid detergent.

44. The composition of claim 43, further comprising one or more enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

45. A composition comprising (i) a detergent; and (ii) the polypeptide of claim 25.

46. The composition of claim 45, wherein the detergent is a liquid detergent.

47. The composition of claim 46, further comprising one or more enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

48. A composition comprising (i) a detergent; and (ii) the polypeptide of claim 26.

49. The composition of claim 48, wherein the detergent is a liquid detergent.

50. The composition of claim 49, further comprising one or more enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

51. A composition comprising (i) a detergent; and (ii) the polypeptide of claim 27.

52. The composition of claim 51, wherein the detergent is a liquid detergent.

53. The composition of claim 52, further comprising one or more enzymes selected from the group consisting of proteases, amylases, cellulases, lipases, xylanases, mannanases, cutinases, pectinases, polygalacturonases, pectate lyases, pectinolytic enzymes, esterases, phytases, arabinases, galactanases, xanthanases, xyloglucanases, DNAses, and oxidases, with or without a mediator.

54. The polypeptide of claim 1, comprising an amino acid sequence having at least 97% identity to the sequence set forth in SEQ ID NO.: 2, wherein the polypeptide comprises amino acid D at position 103, amino acid E at position 105, or amino acid D at position 103 and amino acid E at position 105 in the numbering according to SEQ ID NO: 2.

55. The polypeptide of claim 1, comprising an amino acid sequence having at least 98% identity to the sequence set forth in SEQ ID NO.: 2, wherein the polypeptide comprises amino acid D at position 103, amino acid E at position 105, or amino acid D at position 103 and amino acid E at position 105 in the numbering according to SEQ ID NO: 2.

56. The polypeptide of claim 1, comprising an amino acid sequence having at least 99% identity to the sequence set forth in SEQ ID NO.: 2, wherein the polypeptide comprises amino acid D at position 103, amino acid E at position 105, or amino acid D at position 103 and amino acid E at position 105 in the numbering according to SEQ ID NO: 2.

\* \* \* \* \*

SEQUENCE LISTING

```
<160> NUMBER OF SEQ ID NOS: 12

<210> SEQ ID NO 1
<211> LENGTH: 1004
<212> TYPE: DNA
<213> ORGANISM: Malbranchea cinnamomea
<220> FEATURE:
<221> NAME/KEY: misc_feature
<223> OTHER INFORMATION: mature protease nucleotide sequence

<400> SEQUENCE: 1
gcattggtga cgcagagtaa tgcaccatcc tggggccttg gccgtatttc caaccgacag      60
gctggtattc gtgattacca ctacgatgac tccgccggtg aaggcgtcat cgtctatgat     120
gttgacaccg gcattgacat cagccatccg gatttcgagg gccgtgctat atggggttcc     180
aaccatgtcg accgcgttaa ccaggatcag aatggccatg gacacacgt tgctggtact      240 attggtggaa gggcgtacgg agtcgccaag aaggccacaa tagtggctgt caaggttctc     300
gacgcccagg ggtcaggtac tatcagcggt attattgctg gtcttgactg gagtgtcaat     360
catgctcgac agaatggagt cactagaaga gcggctttga acatgagcct tggcggtggg     420
```

-continued

```
cgcagtatct ctttcaatca ggctgctgca agtgctgtcc aagccggatt gttcgtcgcg    480
gttgctgccg gaaatgaagg ggtaagtgac ttctttctgg cccctcctat ccgtacctgc    540
agaagctaac cagattgctc ttattttttt tcttttttca aaatatagca aaatgcaggt    600
aacacttccc cagcctcaga gccttctgtt tgcacagtag gggcaacctc atcgaatgat    660
gccgccacat cctggtccaa ctatggctca gttggtacgt agggctcggt tttatttatt    720
acttcttccc cacatgcgat cagaccggcc gctgactata tttagttgac gtttacgctc    780
ccggagacgc aattgtctct acctggcccg gtggcggttc caggtctctc tcaggcacat    840
cgatggcttc tccacacgtc gccggcctgg gtgcatacct catcgctctg gagggcatta    900
gcggaggcag tgtatgtgac cgtatcaaag agctggctca acctgtcgtc cagcctggtc    960
caggcaccac caaccgtctt atctacaacg gcagtggccg ctaa                    1004
```

<210> SEQ ID NO 2
<211> LENGTH: 281
<212> TYPE: PRT
<213> ORGANISM: Malbranchea cinnamomea
<220> FEATURE:
<221> NAME/KEY: MISC_FEATURE
<223> OTHER INFORMATION: mature protease amino acid sequence

<400> SEQUENCE: 2

```
Ala Leu Val Thr Gln Ser Asn Ala Pro Ser Trp Gly Leu Gly Arg Ile
1               5                   10                  15

Ser Asn Arg Gln Ala Gly Ile Arg Asp Tyr His Tyr Asp Asp Ser Ala
            20                  25                  30

Gly Glu Gly Val Ile Val Tyr Asp Val Asp Thr Gly Ile Asp Ile Ser
        35                  40                  45

His Pro Asp Phe Glu Gly Arg Ala Ile Trp Gly Ser Asn His Val Asp
    50                  55                  60

Arg Val Asn Gln Asp Gln Asn Gly His Gly Thr His Val Ala Gly Thr
65                  70                  75                  80

Ile Gly Gly Arg Ala Tyr Gly Val Ala Lys Lys Ala Thr Ile Val Ala
                85                  90                  95

Val Lys Val Leu Asp Ala Gln Gly Ser Gly Thr Ile Ser Gly Ile Ile
            100                 105                 110

Ala Gly Leu Asp Trp Ser Val Asn His Ala Arg Gln Asn Gly Val Thr
        115                 120                 125

Arg Arg Ala Ala Leu Asn Met Ser Leu Gly Gly Gly Arg Ser Ile Ser
    130                 135                 140

Phe Asn Gln Ala Ala Ala Ser Ala Val Gln Ala Gly Leu Phe Val Ala
145                 150                 155                 160

Val Ala Ala Gly Asn Glu Gly Gln Asn Ala Gly Asn Thr Ser Pro Ala
                165                 170                 175

Ser Glu Pro Ser Val Cys Thr Val Gly Ala Thr Ser Ser Asn Asp Ala
            180                 185                 190

Ala Thr Ser Trp Ser Asn Tyr Gly Ser Val Val Asp Val Tyr Ala Pro
        195                 200                 205

Gly Asp Ala Ile Val Ser Thr Trp Pro Gly Gly Ser Arg Ser Leu
    210                 215                 220

Ser Gly Thr Ser Met Ala Ser Pro His Val Ala Gly Leu Gly Ala Tyr
225                 230                 235                 240

Leu Ile Ala Leu Glu Gly Ile Ser Gly Gly Ser Val Cys Asp Arg Ile
                245                 250                 255
```

```
Lys Glu Leu Ala Gln Pro Val Val Gln Pro Gly Pro Gly Thr Thr Asn
            260                 265                 270

Arg Leu Ile Tyr Asn Gly Ser Gly Arg
            275                 280

<210> SEQ ID NO 3
<211> LENGTH: 1004
<212> TYPE: DNA
<213> ORGANISM: Malbranchea cinnamomea
<220> FEATURE:
<221> NAME/KEY: misc_feature
<223> OTHER INFORMATION: M59 mature nucleotide sequence
<220> FEATURE:
<221> NAME/KEY: misc_feature
<222> LOCATION: (309)..(309)
<223> OTHER INFORMATION: r = t or c

<400> SEQUENCE: 3
gcattggtga cgcagagtaa tgcaccatcc tggggccttg gccgtatttc caaccgacag      60
gctggtattc gtgattacca ctacgatgac tccgccggtg aaggcgtcat cgtctatgat     120
gttgacaccg gcattgacat cagccatccg gatttcgagg gccgtgctat atggggttcc     180
aaccatgtcg accgcgttaa ccaggatcag aatggccatg gacacacgt tgctggtact      240 attggtggaa gggcgtacgg agtcgccaag aaggccacaa tagtggctgt caaggttctc     300
gacgccgarg gtcaggtac tatcagcggt attattgctg tcttgactg gagtgtcaat       360 catgctcgac agaatggagt cactagaaga gcggctttga acatgagcct tggcggtggg    420
cgcagtatct ctttcaatca ggctgctgca agtgctgtcc aagccggatt gttcgtcgcg    480
gttgctgccg gaaatgaagg ggtaagtgac ttctttctgg ccctcctat ccgtacctgc      540 agaagctaac cagattgctc ttattttttt tctttttca aaatatagca aaatgcaggt     600
aacacttccc cagcctcaga gccttctgtt tgcacagtag gggcaacctc atcgaatgat    660
gccgccacat cctggtccaa ctatggctca gttggtacgt agggctcggt tttatttatt    720
acttcttccc cacatgcgat cagaccggcc gctgactata tttagttgac gtttacgctc    780
ccggagacgc aattgtctct acctggcccg gtggcggttc caggtctctc tcaggcacat    840
cgatggcttc tccacacgtc gccggcctgg gtgcatacct catcgctctg agggcatta    900 gcggaggcag tgtatgtgac cgtatcaaag agctggctca acctgtcgtc cagcctggtc    960
caggcaccac caaccgtctt atctacaacg gcagtggccg ctaa                    1004

<210> SEQ ID NO 4
<211> LENGTH: 281
<212> TYPE: PRT
<213> ORGANISM: Malbranchea cinnamomea
<220> FEATURE:
<221> NAME/KEY: MISC_FEATURE
<223> OTHER INFORMATION: M59 mature amino acid sequence

<400> SEQUENCE: 4

Ala Leu Val Thr Gln Ser Asn Ala Pro Ser Trp Gly Leu Gly Arg Ile
 1               5                  10                  15

Ser Asn Arg Gln Ala Gly Ile Arg Asp Tyr His Tyr Asp Asp Ser Ala
            20                  25                  30

Gly Glu Gly Val Ile Val Tyr Asp Val Asp Thr Gly Ile Asp Ile Ser
        35                  40                  45

His Pro Asp Phe Glu Gly Arg Ala Ile Trp Gly Ser Asn His Val Asp
    50                  55                  60

Arg Val Asn Gln Asp Gln Asn Gly His Gly Thr His Val Ala Gly Thr
```

```
              65                  70                  75                  80
Ile Gly Gly Arg Ala Tyr Gly Val Ala Lys Lys Ala Thr Ile Val Ala
                    85                  90                  95

Val Lys Val Leu Asp Ala Asp Gly Ser Gly Thr Ile Ser Gly Ile Ile
                    100                 105                 110

Ala Gly Leu Asp Trp Ser Val Asn His Ala Arg Gln Asn Gly Val Thr
                    115                 120                 125

Arg Arg Ala Ala Leu Asn Met Ser Leu Gly Gly Arg Ser Ile Ser
            130                 135                 140

Phe Asn Gln Ala Ala Ala Ser Ala Val Gln Ala Gly Leu Phe Val Ala
145                 150                 155                 160

Val Ala Ala Gly Asn Glu Gly Gln Asn Ala Gly Asn Thr Ser Pro Ala
                    165                 170                 175

Ser Glu Pro Ser Val Cys Thr Val Gly Ala Thr Ser Ser Asn Asp Ala
                    180                 185                 190

Ala Thr Ser Trp Ser Asn Tyr Gly Ser Val Val Asp Val Tyr Ala Pro
                    195                 200                 205

Gly Asp Ala Ile Val Ser Thr Trp Pro Gly Gly Ser Arg Ser Leu
            210                 215                 220

Ser Gly Thr Ser Met Ala Ser Pro His Val Ala Gly Leu Gly Ala Tyr
225                 230                 235                 240

Leu Ile Ala Leu Glu Gly Ile Ser Gly Gly Ser Val Cys Asp Arg Ile
                    245                 250                 255

Lys Glu Leu Ala Gln Pro Val Val Gln Pro Gly Pro Gly Thr Thr Asn
                    260                 265                 270

Arg Leu Ile Tyr Asn Gly Ser Gly Arg
            275                 280

<210> SEQ ID NO 5
<211> LENGTH: 1004
<212> TYPE: DNA
<213> ORGANISM: Malbranchea cinnamomea
<220> FEATURE:
<221> NAME/KEY: misc_feature
<223> OTHER INFORMATION: M60 mature nucleotide sequence
<220> FEATURE:
<221> NAME/KEY: misc_feature
<222> LOCATION: (315)..(315)
<223> OTHER INFORMATION: y is g or a

<400> SEQUENCE: 5
gcattggtga cgcagagtaa tgcaccatcc tggggccttg gccgtatttc caaccgacag      60
gctggtattc gtgattacca ctacgatgac tccgccggtg aaggcgtcat cgtctatgat     120
gttgacaccg gcattgacat cagccatccg gatttcgagg gccgtgctat atgggggttcc    180 aaccatgtcg accgcgttaa ccaggatcag aatggccatg gacacacgt tgctggtact     240 attggtggaa gggcgtacgg agtcgccaag aaggccacaa tagtggctgt caaggttctc     300
gacgcccagg gggayggtac tatcagcggt attattgctg tcttgactg gagtgtcaat     360 catgctcgac agaatggagt cactagaaga gcggctttga acatgagcct tggcggtggg    420
cgcagtatct ctttcaatca ggctgctgca agtgctgtcc aagccggatt gttcgtcgcg    480
gttgctgccg gaaatgaagg ggtaagtgac ttctttctgg cccctcctat ccgtacctgc    540
agaagctaac cagattgctc ttatttttt tcttttttca aaatatagca aaatgcaggt     600
aacacttccc cagcctcaga gccttctgtt tgcacagtag gggcaacctc atcgaatgat    660
gccgccacat cctggtccaa ctatggctca gttggtacgt agggctcggt tttatttatt    720
```

```
acttcttccc cacatgcgat cagaccggcc gctgactata tttagttgac gtttacgctc    780
ccggagacgc aattgtctct acctggcccg gtggcggttc caggtctctc tcaggcacat    840
cgatggcttc tccacacgtc gccggcctgg gtgcatacct catcgctctg gagggcatta    900
gcggaggcag tgtatgtgac cgtatcaaag agctggctca acctgtcgtc cagcctggtc    960
caggcaccac caaccgtctt atctacaacg gcagtggccg ctaa                   1004
```

<210> SEQ ID NO 6
<211> LENGTH: 281
<212> TYPE: PRT
<213> ORGANISM: Malbranchea cinnamomea
<220> FEATURE:
<221> NAME/KEY: MISC_FEATURE
<223> OTHER INFORMATION: M60 mature amino acid sequence

<400> SEQUENCE: 6

```
Ala Leu Val Thr Gln Ser Asn Ala Pro Ser Trp Gly Leu Gly Arg Ile
1               5                   10                  15

Ser Asn Arg Gln Ala Gly Ile Arg Asp Tyr His Tyr Asp Ser Ala
            20                  25                  30

Gly Glu Gly Val Ile Val Tyr Asp Val Asp Thr Gly Ile Asp Ile Ser
        35                  40                  45

His Pro Asp Phe Glu Gly Arg Ala Ile Trp Gly Ser Asn His Val Asp
    50                  55                  60

Arg Val Asn Gln Asp Gln Asn Gly His Gly Thr His Val Ala Gly Thr
65                  70                  75                  80

Ile Gly Gly Arg Ala Tyr Gly Val Ala Lys Lys Ala Thr Ile Val Ala
                85                  90                  95

Val Lys Val Leu Asp Ala Gln Gly Glu Gly Thr Ile Ser Gly Ile Ile
            100                 105                 110

Ala Gly Leu Asp Trp Ser Val Asn His Ala Arg Gln Asn Gly Val Thr
        115                 120                 125

Arg Arg Ala Ala Leu Asn Met Ser Leu Gly Gly Gly Arg Ser Ile Ser
130                 135                 140

Phe Asn Gln Ala Ala Ala Ser Ala Val Gln Ala Gly Leu Phe Val Ala
145                 150                 155                 160

Val Ala Ala Gly Asn Glu Gly Gln Asn Ala Gly Asn Thr Ser Pro Ala
                165                 170                 175

Ser Glu Pro Ser Val Cys Thr Val Gly Ala Thr Ser Ser Asn Asp Ala
            180                 185                 190

Ala Thr Ser Trp Ser Asn Tyr Gly Ser Val Val Asp Val Tyr Ala Pro
        195                 200                 205

Gly Asp Ala Ile Val Ser Thr Trp Pro Gly Gly Ser Arg Ser Leu
    210                 215                 220

Ser Gly Thr Ser Met Ala Ser Pro His Val Ala Gly Leu Gly Ala Tyr
225                 230                 235                 240

Leu Ile Ala Leu Glu Gly Ile Ser Gly Gly Ser Val Cys Asp Arg Ile
                245                 250                 255

Lys Glu Leu Ala Gln Pro Val Val Gln Pro Gly Pro Gly Thr Thr Asn
            260                 265                 270

Arg Leu Ile Tyr Asn Gly Ser Gly Arg
        275                 280
```

<210> SEQ ID NO 7
<211> LENGTH: 1004

```
<212> TYPE: DNA
<213> ORGANISM: Malbranchea cinnamomea
<220> FEATURE:
<221> NAME/KEY: misc_feature
<223> OTHER INFORMATION: M61 mature nucleotide sequence
<220> FEATURE:
<221> NAME/KEY: misc_feature
<222> LOCATION: (309)..(309)
<223> OTHER INFORMATION: r is t or c
<220> FEATURE:
<221> NAME/KEY: misc_feature
<222> LOCATION: (315)..(315)
<223> OTHER INFORMATION: y is g or a

<400> SEQUENCE: 7
gcattggtga cgcagagtaa tgcaccatcc tggggccttg gccgtatttc caaccgacag     60
gctggtattc gtgattacca ctacgatgac tccgccggtg aaggcgtcat cgtctatgat    120
gttgacaccg gcattgacat cagccatccg gatttcgagg ccgtgctat atggggttcc    180 aaccatgtcg accgcgttaa ccaggatcag aatggccatg gacacacgt tgctggtact    240 attggtggaa gggcgtacgg agtcgccaag aaggccacaa tagtggctgt caaggttctc    300
gacgccgarg gggayggtac tatcagcggt attattgctg tcttgactg gagtgtcaat    360 catgctcgac agaatggagt cactagaaga gcggctttga acatgagcct tggcggtggg    420
cgcagtatct ctttcaatca ggctgctgca agtgctgtcc aagccggatt gttcgtcgcg    480
gttgctgccg gaaatgaagg ggtaagtgac ttctttctgg cccctcctat ccgtacctgc    540
agaagctaac cagattgctc ttatttttt tcttttttca aaatatagca aaatgcaggt    600
aacacttccc cagcctcaga gccttctgtt tgcacagtag gggcaacctc atcgaatgat    660
gccgccacat cctggtccaa ctatggctca gttggtacgt agggctcggt tttatttatt    720
acttcttccc cacatgcgat cagaccggcc gctgactata tttagttgac gtttacgctc    780
ccggagacgc aattgtctct acctggcccg gtggcggttc caggtctctc tcaggcacat    840
cgatggcttc tccacacgtc gccggcctgg gtgcatacct catcgctctg agggcatta    900 gcggaggcag tgtatgtgac cgtatcaaag agctggctca acctgtcgtc cagcctggtc    960
caggcaccac caaccgtctt atctacaacg gcagtggccg ctaa                   1004

<210> SEQ ID NO 8
<211> LENGTH: 281
<212> TYPE: PRT
<213> ORGANISM: Malbranchea cinnamomea
<220> FEATURE:
<221> NAME/KEY: MISC_FEATURE
<223> OTHER INFORMATION: M61 mature amino acid sequence

<400> SEQUENCE: 8

Ala Leu Val Thr Gln Ser Asn Ala Pro Ser Trp Gly Leu Gly Arg Ile
1               5                   10                  15

Ser Asn Arg Gln Ala Gly Ile Arg Asp Tyr His Tyr Asp Asp Ser Ala
            20                  25                  30

Gly Glu Gly Val Ile Val Tyr Asp Val Asp Thr Gly Ile Asp Ile Ser
        35                  40                  45

His Pro Asp Phe Glu Gly Arg Ala Ile Trp Gly Ser Asn His Val Asp
    50                  55                  60

Arg Val Asn Gln Asp Gln Asn Gly His Gly Thr His Val Ala Gly Thr
65                  70                  75                  80

Ile Gly Gly Arg Ala Tyr Gly Val Ala Lys Lys Ala Thr Ile Val Ala
                85                  90                  95
```

```
Val Lys Val Leu Asp Ala Asp Gly Glu Gly Thr Ile Ser Gly Ile Ile
            100                 105                 110

Ala Gly Leu Asp Trp Ser Val Asn His Ala Arg Gln Asn Gly Val Thr
            115                 120                 125

Arg Arg Ala Ala Leu Asn Met Ser Leu Gly Gly Gly Arg Ser Ile Ser
        130                 135                 140

Phe Asn Gln Ala Ala Ala Ser Ala Val Gln Ala Gly Leu Phe Val Ala
145                 150                 155                 160

Val Ala Ala Gly Asn Glu Gly Gln Asn Ala Gly Asn Thr Ser Pro Ala
                165                 170                 175

Ser Glu Pro Ser Val Cys Thr Val Gly Ala Thr Ser Ser Asn Asp Ala
            180                 185                 190

Ala Thr Ser Trp Ser Asn Tyr Gly Ser Val Val Asp Val Tyr Ala Pro
        195                 200                 205

Gly Asp Ala Ile Val Ser Thr Trp Pro Gly Gly Ser Arg Ser Leu
210                 215                 220

Ser Gly Thr Ser Met Ala Ser Pro His Val Ala Gly Leu Gly Ala Tyr
225                 230                 235                 240

Leu Ile Ala Leu Glu Gly Ile Ser Gly Gly Ser Val Cys Asp Arg Ile
                245                 250                 255

Lys Glu Leu Ala Gln Pro Val Val Gln Pro Gly Pro Gly Thr Thr Asn
            260                 265                 270

Arg Leu Ile Tyr Asn Gly Ser Gly Arg
            275                 280

<210> SEQ ID NO 9
<211> LENGTH: 1436
<212> TYPE: DNA
<213> ORGANISM: Malbranchea cinnamomea
<220> FEATURE:
<221> NAME/KEY: misc_feature
<223> OTHER INFORMATION: The nucleotide sequence encoding the
      full-length amino acid sequence of Malbranchea ALKO4122 protease.
      The full-length gene in included in plasmid pALK3094. The protease
      sequence cloned from Malbranchea ALKO4178 by PCR was identical to
      this sequence.

<400> SEQUENCE: 9
atgggcgtct tcagcaaact cttgtatctg tcttttgcag tcacggcctc tgtcaatgcc      60
ggtgaaatcc tttcagtcgc caacaaggac agtgttatcc ctgacacgta tatcgtggtg    120
ttgaaggaag gagtttcaac ccaggagttc aatgctcata aaaactgggt gaacgagatt    180
catcgcacca acctcacgag gcgtgacctg ggtttcactg gcgagttaaa gcatagctat    240
gattttggtg gacatggact gaagggctac agcggcaagt tgatgccac tgccattcag    300 gaaattgcca atgatcctaa tgtatgcttg ttaagaattc ttcccagcga gatatcttca    360
tgcaagccat gcaattgctg acaggtgaat taggtggcct acgtcgaacc ggaccaggag    420
gtgaagcttg atgcattggt gacgcagagt aatgcaccat cctggggcct tggccgtatt    480
tccaaccgac aggctggtat tcgtgattac cactacgatg actccgccgg tgaaggcgtc    540
atcgtctatg atgttgacac cggtattgac atcagccatc cggatttcga gggccgtgct    600
atatggggtt ccaaccatgt cgaccgcgtt aaccaggatc agaatggcca tgggacacac    660
gttgctggta ctattggtgg aagggcgtac ggagtcgcca agaaggccac aatagtggct    720
gtcaaggttc tcgacgccca gggggtcaggt actatcagcg gtattattgc tggtcttgac    780
tggagtgtca atcatgctcg acagaatgga gtcactagaa gagcggcttt gaacatgagc    840
```

```
cttggcggtg ggcgcagtat ctctttcaat caggctgctg caagtgctgt ccaagccgga    900
ttgttcgtcg cggttgctgc cggaaatgaa ggggtaagtg acttcttcct ggcccctcct    960
atccgtacct gcagaagcta accagattgc tcttattttt tttcttttt caaaatatag    1020 caaaatgcag gtaacacttc cccagcctca gagccttctg tttgcacagt aggggcaacc    1080
tcatcgaatg atgccgccac atcctggtcc aactatggct cagttggtac gtagggctcg    1140
gttttattta ttacttcttc cccacatgcg atcagaccgg ccgctgacta tatttagttg    1200
acgtttacgc tcccggagac gcaattgtct ctacctggcc cggtggcggt tccaggtctc    1260
tctcaggcac atcgatggct ctccacacg tcgccggcct gggtgcatac ctcatcgctc    1320
tggagggcat tagcggaggc agtgtatgtg accgtatcaa agagctggct caacctgtcg    1380
tccagcctgg tccaggcacc accaaccgtc ttatctacaa cggcagtggc cgctaa    1436
```

<210> SEQ ID NO 10
<211> LENGTH: 401
<212> TYPE: PRT
<213> ORGANISM: Malbranchea cinnamomea
<220> FEATURE:
<221> NAME/KEY: MISC_FEATURE
<223> OTHER INFORMATION: The full-length amino acid sequence of
      Malbranchea ALKO4122 protease including amino acids Met1 to Arg
      401 of the full length protease.

<400> SEQUENCE: 10

```
Met Gly Val Phe Ser Lys Leu Leu Tyr Leu Ser Phe Ala Val Thr Ala
1               5                   10                  15

Ser Val Asn Ala Gly Glu Ile Leu Ser Val Ala Asn Lys Asp Ser Val
            20                  25                  30

Ile Pro Asp Thr Tyr Ile Val Leu Lys Glu Gly Val Ser Thr Gln
        35                  40                  45

Glu Phe Asn Ala His Lys Asn Trp Val Asn Glu Ile His Arg Thr Asn
    50                  55                  60

Leu Thr Arg Arg Asp Leu Gly Phe Thr Gly Glu Leu Lys His Ser Tyr
65                  70                  75                  80

Asp Phe Gly Gly His Gly Leu Lys Gly Tyr Ser Gly Lys Phe Asp Ala
                85                  90                  95

Thr Ala Ile Gln Glu Ile Ala Asn Asp Pro Asn Val Ala Tyr Val Glu
            100                 105                 110

Pro Asp Gln Glu Val Lys Leu Asp Ala Leu Val Thr Gln Ser Asn Ala
        115                 120                 125

Pro Ser Trp Gly Leu Gly Arg Ile Ser Asn Arg Gln Ala Gly Ile Arg
    130                 135                 140

Asp Tyr His Tyr Asp Asp Ser Ala Gly Glu Gly Val Ile Val Tyr Asp
145                 150                 155                 160

Val Asp Thr Gly Ile Asp Ile Ser His Pro Asp Phe Glu Gly Arg Ala
                165                 170                 175

Ile Trp Gly Ser Asn His Val Arg Val Asn Asp Gln Asn Gly
            180                 185                 190

His Gly Thr His Val Ala Gly Thr Ile Gly Gly Arg Ala Tyr Gly Val
        195                 200                 205

Ala Lys Lys Ala Thr Ile Val Ala Val Lys Val Leu Asp Ala Gln Gly
    210                 215                 220

Ser Gly Thr Ile Ser Gly Ile Ile Ala Gly Leu Asp Trp Ser Val Asn
225                 230                 235                 240

His Ala Arg Gln Asn Gly Val Thr Arg Arg Ala Ala Leu Asn Met Ser
```

```
                245                 250                 255
Leu Gly Gly Gly Arg Ser Ile Ser Phe Asn Gln Ala Ala Ala Ser Ala
            260                 265                 270

Val Gln Ala Gly Leu Phe Val Ala Val Ala Ala Gly Asn Glu Gly Gln
            275                 280                 285

Asn Ala Gly Asn Thr Ser Pro Ala Ser Glu Pro Ser Val Cys Thr Val
            290                 295                 300

Gly Ala Thr Ser Ser Asn Asp Ala Ala Thr Ser Trp Ser Asn Tyr Gly
305                 310                 315                 320

Ser Val Val Asp Val Tyr Ala Pro Gly Asp Ala Ile Val Ser Thr Trp
                325                 330                 335

Pro Gly Gly Gly Ser Arg Ser Leu Ser Gly Thr Ser Met Ala Ser Pro
            340                 345                 350

His Val Ala Gly Leu Gly Ala Tyr Leu Ile Ala Leu Glu Gly Ile Ser
            355                 360                 365

Gly Gly Ser Val Cys Asp Arg Ile Lys Glu Leu Ala Gln Pro Val Val
            370                 375                 380

Gln Pro Gly Pro Gly Thr Thr Asn Arg Leu Ile Tyr Asn Gly Ser Gly
385                 390                 395                 400

Arg

<210> SEQ ID NO 11
<211> LENGTH: 1546
<212> TYPE: DNA
<213> ORGANISM: Malbranchea cinnamomea

<400> SEQUENCE: 11
tcatgagcag gcaatcccac tcagttcaat tttgttgatc tacattaatc atgggcgtct      60
tcagcaaact cttgtatctg tcttttgcag tcacggcctc tgtcaatgcc ggtgaaatcc     120
tttcagtcgc caacaaggac agtgttatcc ctgacacgta tcgtggtgtg ttgaaggaag     180
gagtttcaac ccaggagttc aatgctcata aaaactgggt gaacgagatt catcgcacca     240
acctcacgag gcgtgacctg ggtttcactg gcgagttaaa gcatagctat gattttggtg     300
gacatggact gaagggctac agcggcaagt tgatgccacc tgccattcag gaaattgcca     360
atgatcctaa tgtatgcttg ttaagaattc ttcccagcga gatatcttca tgcaagccat     420
gcaattgctg acaggtgaat taggtggcct acgtcgaacc ggaccaggag gtgaagcttg     480
atgcattggt gacgcagagt aatgcaccat cctgggggcct tggccgtatt tccaaccgac     540
aggctggtat tcgtgattac cactacgatg actccgccgg tgaaggcgtc atcgtctatg     600
atgttgacac cggtattgac atcagccatc cggatttcga gggccgtgct atatggggtt     660
ccaaccatgt cgaccgcgtt aaccaggatc agaatgccat gggacacac gttgctggta     720 ctattggtgg aagggcgtac ggagtcgcca agaaggccac aatagtggct gtcaaggttc     780
tcgacgccca ggggtcaggt actatcagcg gtattattgc tggtcttgac tggagtgtca     840
atcatgctcg acagaatgga gtcactagaa gagcggcttt gaacatgagc cttggcggtg     900
ggcgcagtat ctcttctcaat caggctgctg caagtgctgt ccaagccgga ttgttcgtcg     960
cggttgctgc cggaaatgaa ggggtaagtg acttcttcct ggcccctcct atccgtacct    1020
gcagaagcta accagattgc tcttatttt tttcttttt caaaatatag caaaatgcag    1080
gtaacacttc cccagcctca gagccttctg tttgcacagt aggggcaacc tcatcgaatg    1140
atgccgccac atcctggtcc aactatggct cagttggtac gtagggctcg gttttattta    1200
```

-continued

```
ttacttcttc cccacatgcg atcagaccgg ccgctgacta tatttagttg acgtttacgc    1260
tcccggagac gcaattgtct ctacctggcc cggtggcggt tccaggtctc tctcaggcac    1320
atcgatggct tctccacacg tcgccggcct gggtgcatac ctcatcgctc tggagggcat    1380
tagcggaggc agtgtatgtg accgtatcaa agagctggct caacctgtcg tccagcctgg    1440
tccaggcacc accaaccgtc ttatctacaa cggcagtggc cgctaaattg atagtagcta    1500
cagaaggcat agggcttgcg gcgactcggg caatgcagga tatttt    1546
```

<210> SEQ ID NO 12
<211> LENGTH: 294
<212> TYPE: PRT
<213> ORGANISM: Malbranchea cinnamomea

<400> SEQUENCE: 12

```
Val Ala Tyr Val Glu Pro Asp Gln Glu Val Lys Leu Asp Ala Leu Val
1               5                   10                  15

Thr Gln Ser Asn Ala Pro Ser Trp Gly Leu Gly Arg Ile Ser Asn Arg
            20                  25                  30

Gln Ala Gly Ile Arg Asp Tyr His Tyr Asp Ser Ala Gly Glu Gly
        35                  40                  45

Val Ile Val Tyr Asp Val Asp Thr Gly Ile Asp Ile Ser His Pro Asp
    50                  55                  60

Phe Glu Gly Arg Ala Ile Trp Gly Ser Asn His Val Asp Arg Val Asn
65                  70                  75                  80

Gln Asp Gln Asn Gly His Gly Thr His Val Ala Gly Thr Ile Gly
                85                  90                  95

Arg Ala Tyr Gly Val Ala Lys Lys Ala Thr Ile Val Ala Val Lys Val
                100                 105                 110

Leu Asp Ala Gln Gly Ser Gly Thr Ile Ser Gly Ile Ile Ala Gly Leu
            115                 120                 125

Asp Trp Ser Val Asn His Ala Arg Gln Asn Gly Val Thr Arg Arg Ala
        130                 135                 140

Ala Leu Asn Met Ser Leu Gly Gly Gly Arg Ser Ile Ser Phe Asn Gln
145                 150                 155                 160

Ala Ala Ala Ser Ala Val Gln Ala Gly Leu Phe Val Ala Val Ala Ala
                165                 170                 175

Gly Asn Glu Gly Gln Asn Ala Gly Asn Thr Ser Pro Ala Ser Glu Pro
            180                 185                 190

Ser Val Cys Thr Val Gly Ala Thr Ser Ser Asn Asp Ala Ala Thr Ser
        195                 200                 205

Trp Ser Asn Tyr Gly Ser Val Val Asp Val Tyr Ala Pro Gly Asp Ala
    210                 215                 220

Ile Val Ser Thr Trp Pro Gly Gly Gly Ser Arg Ser Leu Ser Gly Thr
225                 230                 235                 240

Ser Met Ala Ser Pro His Val Ala Gly Leu Gly Ala Tyr Leu Ile Ala
                245                 250                 255

Leu Glu Gly Ile Ser Gly Gly Ser Val Cys Asp Arg Ile Lys Glu Leu
            260                 265                 270

Ala Gln Pro Val Val Gln Pro Gly Pro Gly Thr Thr Asn Arg Leu Ile
        275                 280                 285

Tyr Asn Gly Ser Gly Arg
    290
```